United States Patent
Hoshino

(10) Patent No.: US 8,808,167 B2
(45) Date of Patent: Aug. 19, 2014

(54) BENDING OPERATION APPARATUS FOR ENDOSCOPE

(71) Applicant: Olympus Medical Systems Corp., Tokyo (JP)

(72) Inventor: Yuki Hoshino, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/066,040

(22) Filed: Oct. 29, 2013

(65) Prior Publication Data

US 2014/0058323 A1    Feb. 27, 2014

Related U.S. Application Data

(63) Continuation of application No. PCT/JP2012/072375, filed on Sep. 3, 2012.

(30) Foreign Application Priority Data

Oct. 28, 2011  (JP) ................................ 2011-237648
Oct. 28, 2011  (JP) ................................ 2011-237649
Oct. 28, 2011  (JP) ................................ 2011-237650

(51) Int. Cl.
*A61B 1/00* (2006.01)
*A61B 1/005* (2006.01)
*A61M 25/01* (2006.01)
*G02B 23/24* (2006.01)

(52) U.S. Cl.
CPC .......... *A61M 25/0147* (2013.01); *A61B 1/0052* (2013.01); *A61B 1/00147* (2013.01); *G02B 23/2476* (2013.01)
USPC ....................................................... 600/146

(58) Field of Classification Search
CPC ................. A61B 1/005; A61B 1/0051; A61B 1/0052–1/0053; A61B 1/0055–1/0057; A61B 1/00147; A61B 1/00149; A61B 1/00151; A61B 1/00154; A61B 1/00156; A61B 17/00491; A61B 2017/003; A61B 2017/00495; A61B 1/00039; A61B 1/00078; A61B 1/0011; A61M 3/0279; A61M 25/0122; A61M 25/0133; A61M 25/0136; A61M 25/0166; A61M 25/1011; A61M 25/0155; A61M 2025/01; A61M 2025/0105; A61M 2025/0133; A61M 2025/015; A61M 2025/0161; G02B 23/2476; F16C 1/14
USPC ..................... 600/146–150; 604/95.01–95.04
See application file for complete search history.

(56) References Cited

U.S. PATENT DOCUMENTS 3,610,231 A * 10/1971 Takahashi et al. ............ 600/139
3,788,303 A *  1/1974 Hall ............................... 600/148
4,207,873 A *  6/1980 Kruy ............................. 600/146

(Continued)

FOREIGN PATENT DOCUMENTS

JP    S60-45337         3/1985
JP    06-327616 A      11/1994

(Continued)

OTHER PUBLICATIONS

International Search Report dated Oct. 2, 2012 issued in PCT/JP2012/072375.

*Primary Examiner* — Manuel Mendez
(74) *Attorney, Agent, or Firm* — Scully, Scott, Murphy & Presser, P.C.

(57) ABSTRACT

A rotation shaft, a bending operation knob, a fixed shaft, two movable disks, a fixed disk, a cam member, a resistance giving member and a fixing lever are included. The resistance giving member has a rocking portion that fixes a rotation position of the cam member in a second position of the movable disks by abutting onto an inner circumferential face of a protruding portion provided at the cam member that moves with rotation of the cam member with an urging force, and is rockable in a diameter direction of the cam member.

10 Claims, 15 Drawing Sheets

(56) References Cited

U.S. PATENT DOCUMENTS 4,688,555 A * 8/1987 Wardle .......................... 600/149
4,726,355 A * 2/1988 Okada ........................... 600/114
5,549,542 A * 8/1996 Kovalcheck .................. 600/146

FOREIGN PATENT DOCUMENTS

| | | |
|---|---|---|
| JP | 07-261098 A | 10/1995 |
| JP | 10-286220 A | 10/1998 |
| JP | 10-295628 A | 11/1998 |
| JP | 2000-152912 A | 6/2000 |
| JP | 2000-166861 A | 6/2000 |
| JP | 2004-351221 A | 12/2004 |
| JP | 2011-182981 A | 9/2011 |

* cited by examiner w2>w1 w3>w1

BENDING OPERATION APPARATUS FOR ENDOSCOPE

CROSS REFERENCE TO RELATED APPLICATION

This application is a continuation application of PCT/JP2012/072375 filed on Sep. 3, 2012 and claims benefit of Japanese Applications No. 2011-237648 filed in Japan on Oct. 28, 2011, No. 2011-237649 filed in Japan on Oct. 28, 2011, No. 2011-237650 filed in Japan on Oct. 28, 2011, the entire contents of which are incorporated herein by this reference.

BACKGROUND OF INVENTION

1. Field of the Invention

The present invention relates to a bending operation apparatus for an endoscope that is provided in an operation portion of the endoscope, and causes a bending portion of an insertion portion of the endoscope to bend.

2. Description of the Related Art

In recent years, endoscopes have been widely used in medical fields and industrial fields. The endoscopes for use in the medical fields are capable of observing organs in body cavities and performing various treatments with use of treatment instruments inserted into insertion channels for the treatment instruments that are included in the endoscopes in accordance with necessity, by elongated insertion portions being inserted into body cavities that are subjects.

Further, the endoscopes for use in the industrial fields are capable of performing inspection such as observation of flaws, corrosion and the like of sites to be examined in objects and various treatments, by elongated insertion portions of the endoscopes being inserted into objects such as jet engines and piping of factories.

Here, a configuration in which a bending portion bendable in a plurality of directions is provided at the insertion portion of an endoscope is known. The bending portion not only enhances the advance ability of the insertion portion in a crooked portion in a duct, but also makes the observation direction of an observation optical system variable, the observation optical system being provided at a distal end portion located at a distal end side in an insertion direction from the bending portion, in the insertion portion.

Normally, the bending portion provided at the insertion portion of an endoscope is configured to be bendable in four directions, up and down, and left and right, for example, by a plurality of bending pieces being connected along the insertion direction of the insertion portion.

Further, the bending portion is bendable in any one of the up and down and left and right directions, by a bending operation apparatus, which is provided in the operation portion, performing a pulling operation of any one of four wires which have distal ends fixed to the bending piece that is located at the most distal end side in the insertion direction out of the bending pieces, the wires being inserted through the inside of the insertion portion.

More specifically, the bending portion has a configuration in which a bending operation knob for vertical bending that is provided in the operation portion is rotationally operated, whereby a sprocket for vertical bending that is provided in the operation portion is rotated, any one of an upper side chain site and a lower side chain site of a vertical bending chain that is wound around the sprocket is pulled, whereby any one of the upper and lower wires is pulled, so that the bending portion is bent in either an up direction or a down direction.

Further, the bending portion has a configuration in which the bending operation knob for lateral bending that is provided in the operation portion is rotationally operated, whereby a sprocket for lateral bending that is provided in the operation portion is rotated, and any one of a left side chain site and a right side chain site of a lateral bending chain that is wound around the sprocket is pulled, whereby any one of a left and a right wires is pulled, so that the bending portion is bent in either a left direction or a right direction.

Further, the configuration is known, in which the operation portion is provided with a vertical bending fixing lock lever that fixes the bending angle of the bending portion that is bent in an up direction or a down direction by a rotational operation of a bending operation knob for vertical bending, namely, a rotation position of the bending operation knob for vertical bending. Furthermore, a configuration is also known in which the operation portion is provided with a lateral bending fixing lock knob that fixes the bending angle of the bending portion that is bent in a left direction or a right direction by a rotational operation of a bending operation knob for lateral bending, namely, the rotation position of the bending operation knob for lateral bending. The configurations are disclosed in Japanese Patent Application Laid-Open Publication No. 2000-152912, Japanese Patent Application Laid-Open Publication No. 7-261098 and Japanese Patent Application Laid-Open Publication No. 10-295628.

Furthermore, Japanese Patent Application Laid-Open Publication No. 6-327616 discloses the configuration in which a locking member that prevents unintentional motion of the fixing operation member is provided in either the operation portion of an endoscope or the fixing operation member.

Furthermore, Japanese Patent Application Laid-Open Publication No. 2004-351221 discloses the configuration in which with use of an O-ring, the fixing operation member and the bending operation knob simultaneously rotate.

SUMMARY OF THE INVENTION

A bending operation apparatus for an endoscope according to one aspect of the present invention includes a rotation shaft, a bending operation knob that is rotatable with the rotation shaft, and performs a bending operation of a bending portion of an endoscope, a fixed shaft that is provided on a same axis as the rotation shaft in an axial direction of the rotation shaft, and is irrotational with respect to the rotation shaft, a fixed disk that includes a first surface and a second surface, and rotates with rotation of the bending operation knob, two movable disks including a first movable disk provided at a side of the first surface of the fixed disk, and a second movable disk provided at a side of the second surface of the fixed disk, a moving member that is located on a same axis in the axial direction as the two movable disks, and moves the first movable disk or the second movable disk to a first position where the two movable disks are separated by a first space by rotation of the moving member, and a second position where the two movable disks are separated by a second space that is shorter than the first space and at which the two movable disks sandwich the fixed disk by respectively abutting on the fixed disk, a resistance giving member that is fixed to an outer periphery of the fixed shaft, is provided in an inner side of the moving member, and gives a resistance force to rotation of the moving member, and a fixing operation member that performs the rotational operation of the moving member, wherein the resistance giving member has a rocking portion that fixes a rotation position of the moving member in the second position of the movable disk by abutting onto an inner circumferential face of the protruding portion provided at the moving member that moves with the rotation of the moving member, with an urging force, and is rockable in a diameter direction of the moving member.

DETAILED DESCRIPTION OF THE PREFERRED EMBODIMENT(S)

Hereinafter, an embodiment of the present invention will be described with reference to the drawings.

Figure 1:
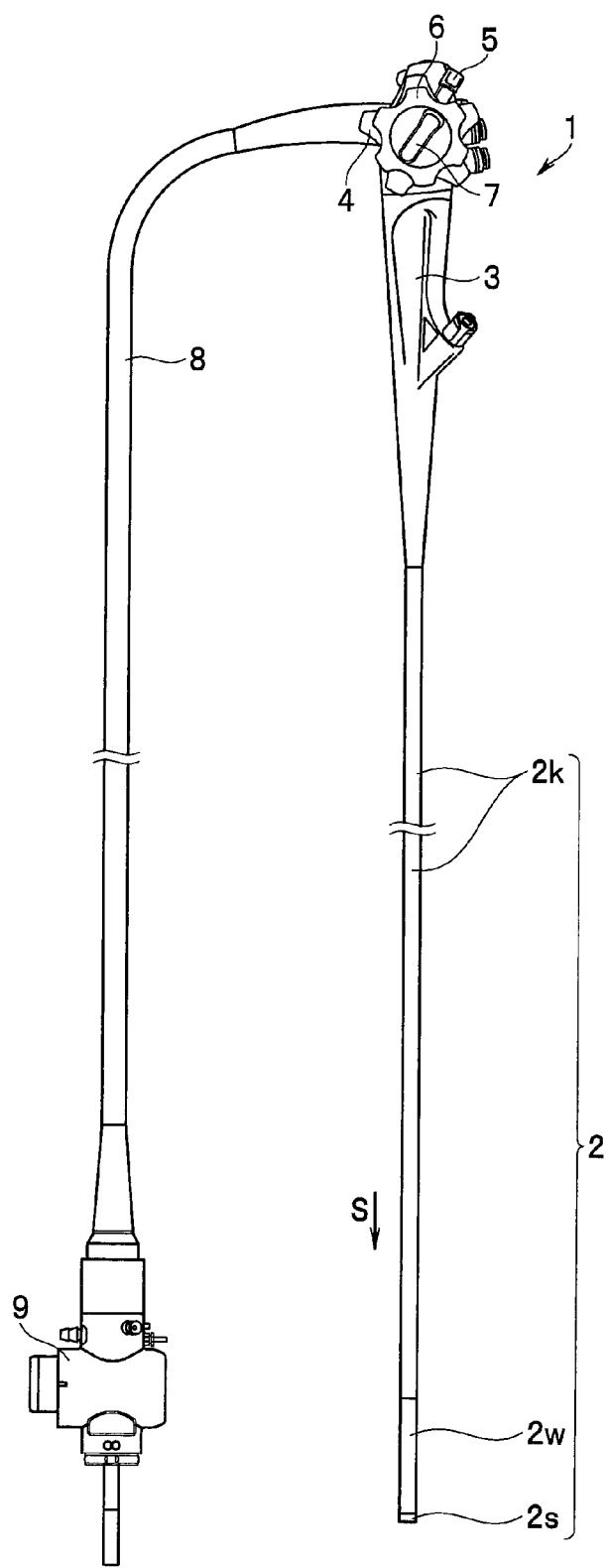
FIG. 1 is a view showing an external appearance of an endoscope including a bending operation apparatus of a present embodiment in an operation portion.

FIG. 1 is a view showing an external appearance of an endoscope including a bending operation apparatus of the present embodiment in an operation portion.

As shown in FIG. 1, an endoscope 1 has a main part configured by including an insertion portion 2 that is inserted into a subject, an operation portion 3 that is connectively provided at a proximal end side in an insertion direction S of the insertion portion 2, a universal cord 8 that is extended from the operation portion 3, and a connector 9 that is provided at an extended end of the universal cord 8. Note that the endoscope 1 is electrically connected to outside apparatuses such as a control apparatus and an illumination apparatus via the connector 9.

The operation portion 3 is provided with a vertical bending operation knob (hereinafter, simply called a bending operation knob) 4 that causes a bending portion 2w, which will be described later, of the insertion portion 2 to bend in a vertical direction, and a lateral bending operation knob (hereinafter, simply called a bending operation knob) 6 that causes the bending portion 2w to bend in a lateral direction.

Furthermore, the operation portion 3 is provided with a fixing lever 5 that is a fixing operation member that fixes a rotation position of the bending operation knob 4, and a fixing knob 7 that is a fixing operation member that fixes a rotation position of the bending operation knob 6.

Note that the bending operation knob 4, the fixing lever 5, the bending operation knob 6 and the fixing knob 7 configure a bending operation apparatus 100 (see FIG. 2), which will be described later in the present embodiment, together with other members provided in the operation portion 3.

The insertion portion 2 is configured by a distal end portion 2s, the bending portion 2w and a flexible tube portion 2k, and is formed to be elongated along the insertion direction S.

In the distal end portion 2s, an image pickup unit (not illustrated) that observes an inside of a subject, an illumination unit that illuminates an inside of a subject, and the like are provided.

Further, the bending portion 2w makes an observation direction of the image pickup unit provided at the distal end portion 2s variable and enhances insertability of the distal end portion 2s in a subject, by being bent in, for example, four directions of up and down and left and right by rotational operations of the bending operation knob 4 and the bending operation knob 6. Furthermore, at a proximal end side of the bending portion 2w, the flexible tube portion 2k is connectively provided.

Next, a configuration of the bending operation apparatus 100 for an endoscope which is provided in the operation portion 3 will be described with use of FIG. 2 to FIG. 19.

Figure 2:
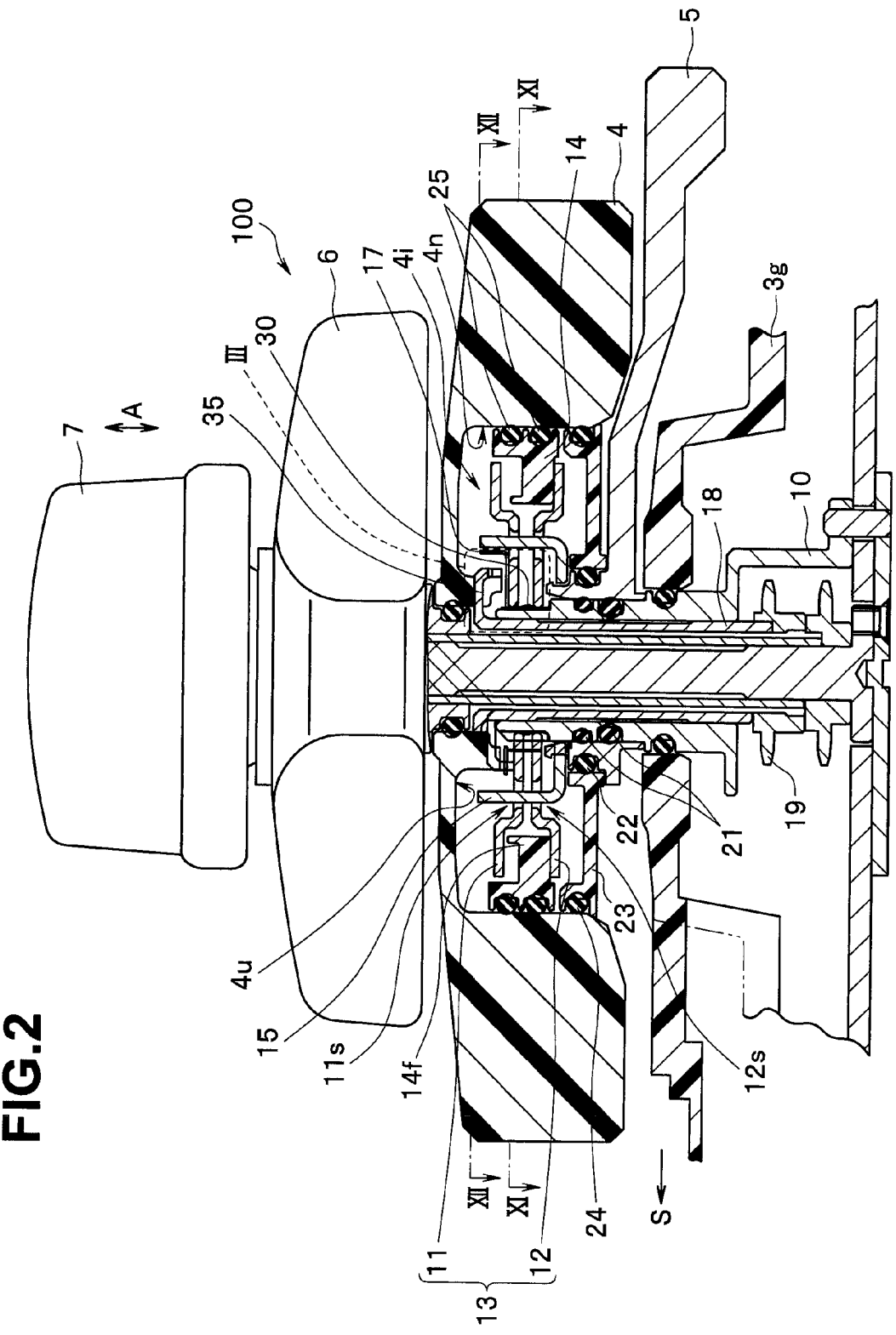
FIG. 2 is a partial sectional view showing a configuration of the bending operation apparatus provided in the operation portion of the endoscope of FIG. 1.
Figure 3:
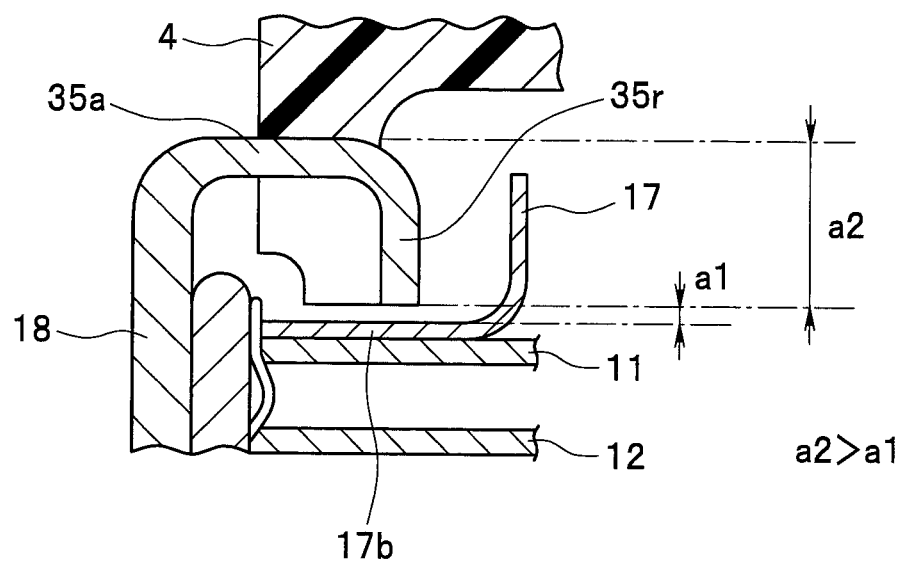
FIG. 3 is a partial sectional view showing a site enclosed by the III line in FIG. 2 under enlargement.
Figure 4:
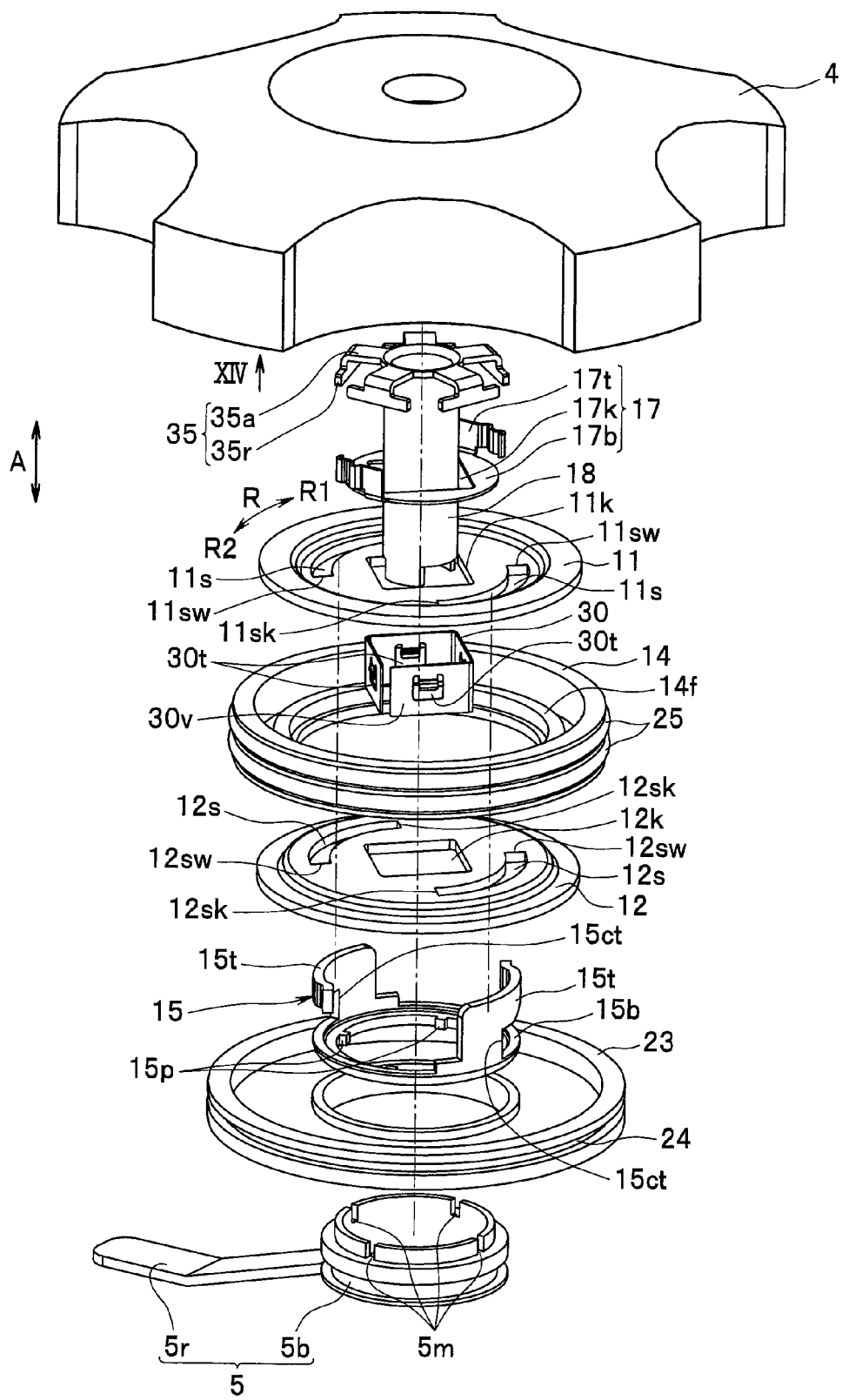
FIG. 4 is an exploded perspective view showing a configuration of a part of the bending operation apparatus in FIG. 2.

FIG. 2 is a partial sectional view showing a configuration of the bending operation apparatus provided in the operation portion of the endoscope of FIG. 1. FIG. 3 is a partial sectional view showing a site enclosed by the III line in FIG. 2 under enlargement. FIG. 4 is an exploded perspective view showing a configuration of a part of the bending operation apparatus in FIG. 2.

Figure 5:
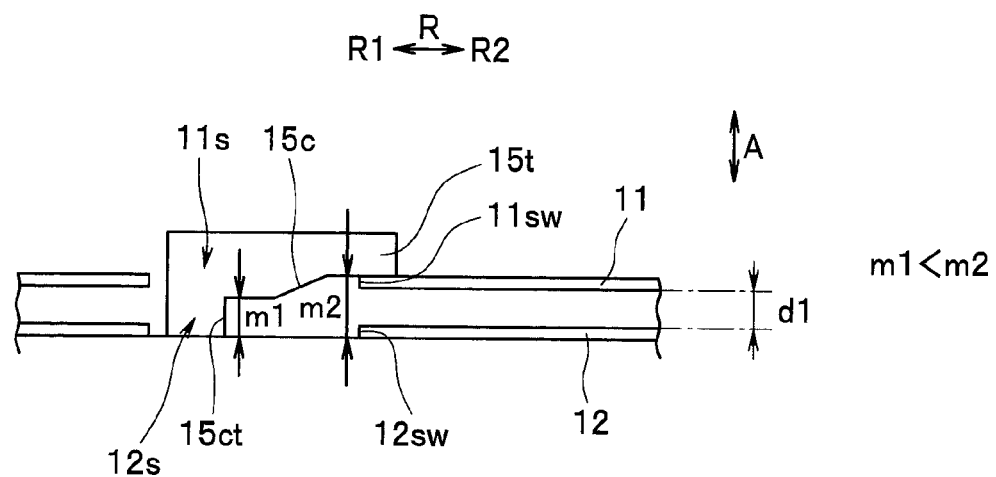
FIG. 5 is a view schematically showing a state in which parts of two movable disks are assembled to be fitted in a cam groove provided in a protruding portion of a cam member of FIG. 4 by having a first space therebetween.
Figure 6:
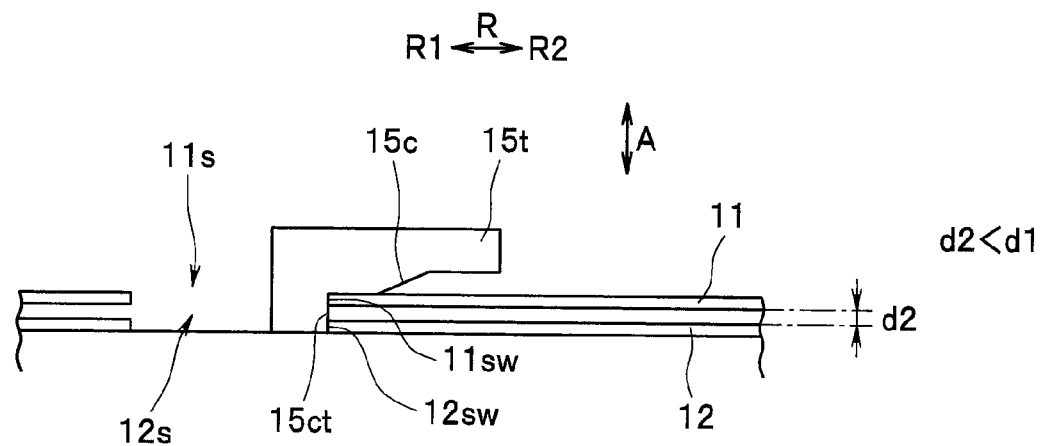
FIG. 6 is a view schematically showing a state in which the two movable disks in FIG. 5 move to a second space by the cam groove with rotation of the cam member.

Further, FIG. 5 is a view schematically showing a state in which parts of two movable disks are assembled to be fitted in a cam groove provided in a protruding portion of a cam member of FIG. 4 by having a first space therebetween. FIG. 6 is a view schematically showing a state in which the two movable disks of FIG. 5 move to a second space by the cam groove with rotation of the cam member.

Figure 7:
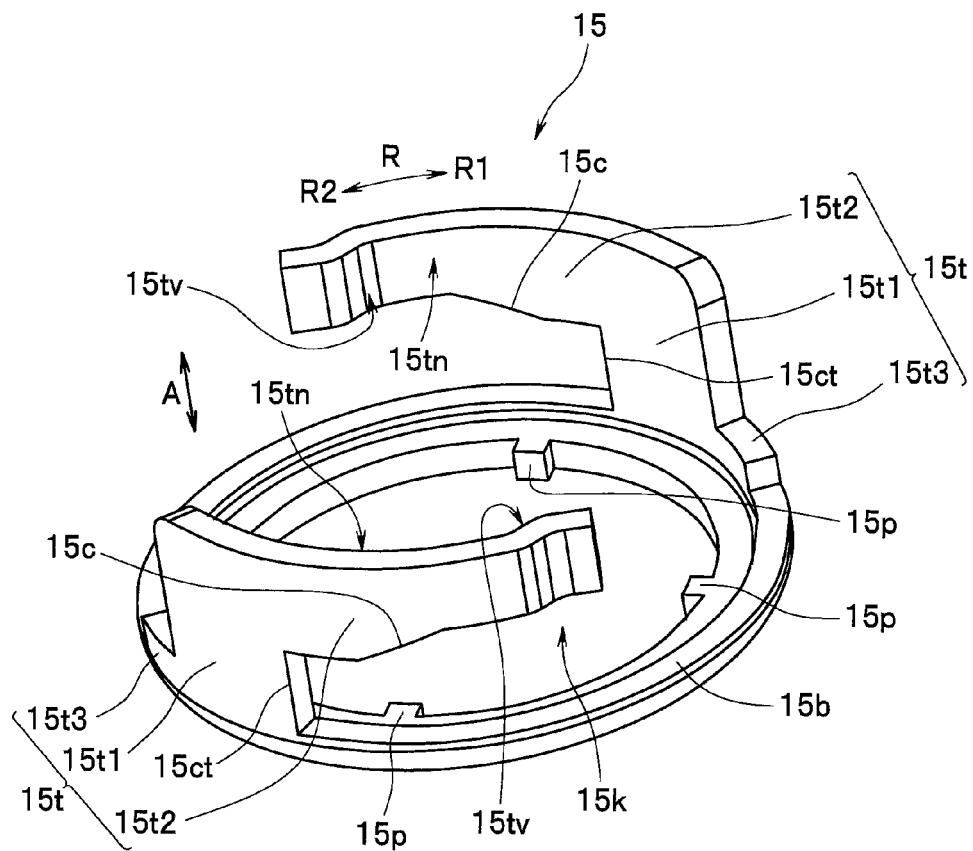
FIG. 7 is a perspective view showing the cam member of FIG. 4 under enlargement.
Figure 8:
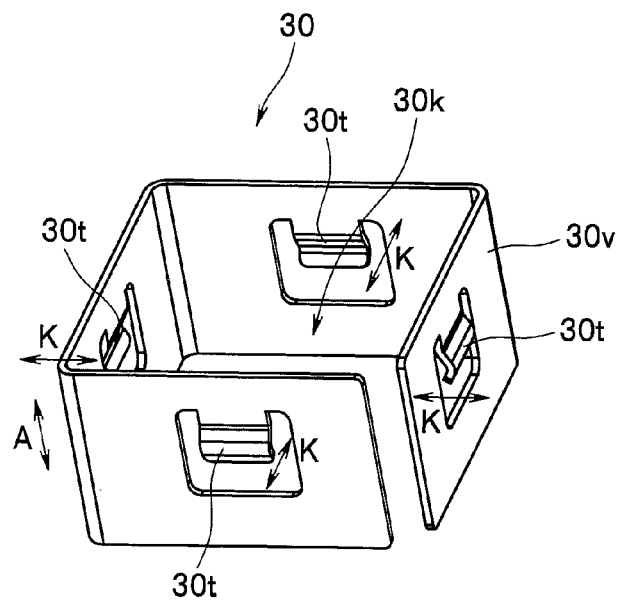
FIG. 8 is a perspective view showing a positioning spring of FIG. 4 under enlargement.
Figure 9:
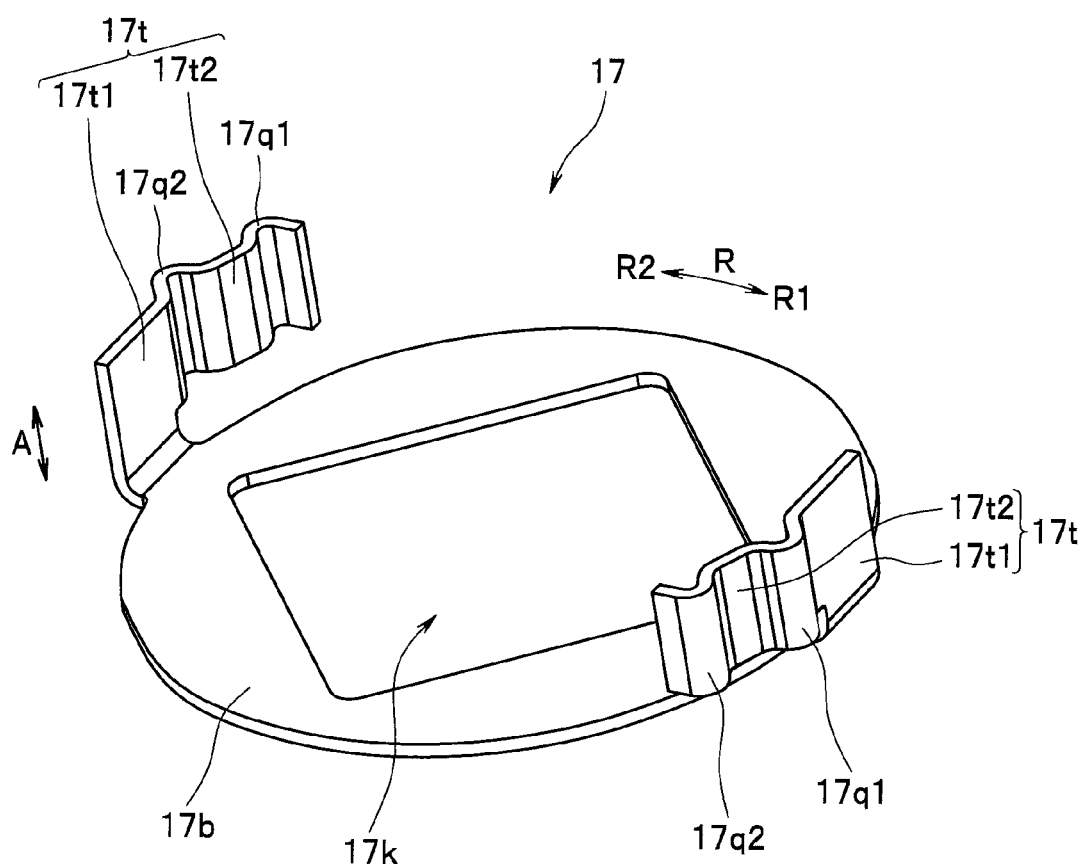
FIG. 9 is a perspective view showing a resistance giving member of FIG. 4 under enlargement.

Furthermore, FIG. 7 is a perspective view showing the cam member of FIG. 4 under enlargement. FIG. 8 is a perspective view showing a positioning spring of FIG. 4 under enlargement. FIG. 9 is a perspective view showing a resistance giving member of FIG. 4 under enlargement.

Figure 10:
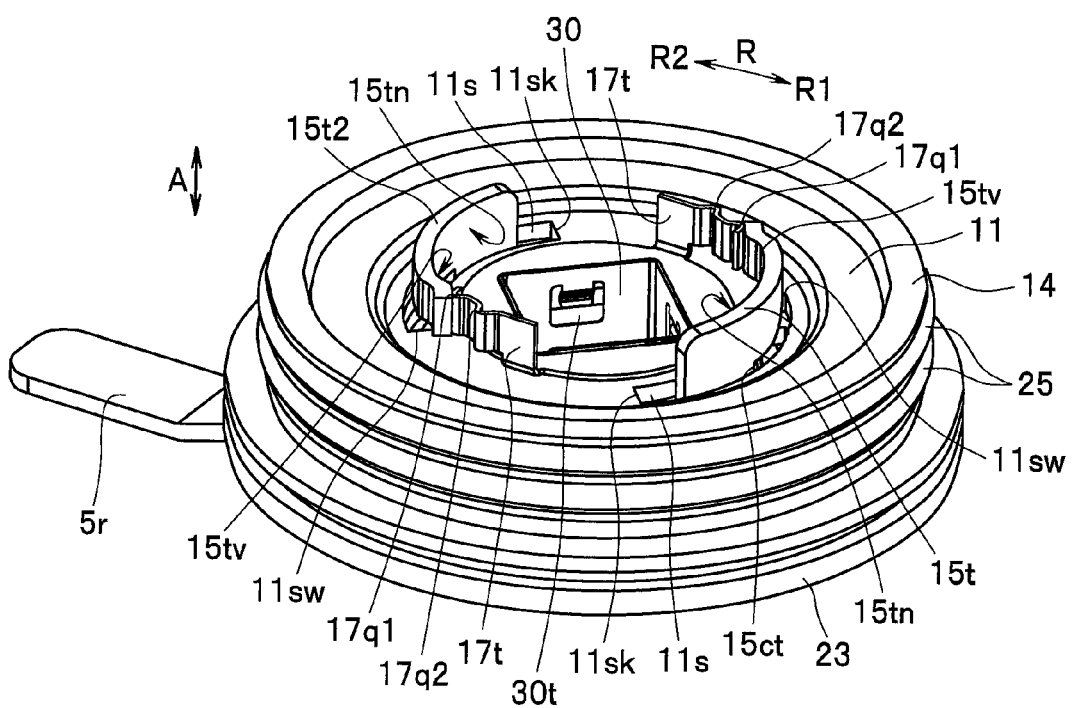
FIG. 10 is a perspective view showing a state in which the cam member, the resistance giving member, the two movable disks, a fixed disk, the positioning spring, a support plate and a fixing lever of FIG. 4 are assembled under enlargement.

Further, FIG. 10 is a perspective view showing a state in which the cam member, the resistance giving member, the two movable disks, a fixed disk, the positioning spring, a support plate and the fixing lever of FIG. 4 are assembled.

Figure 11:
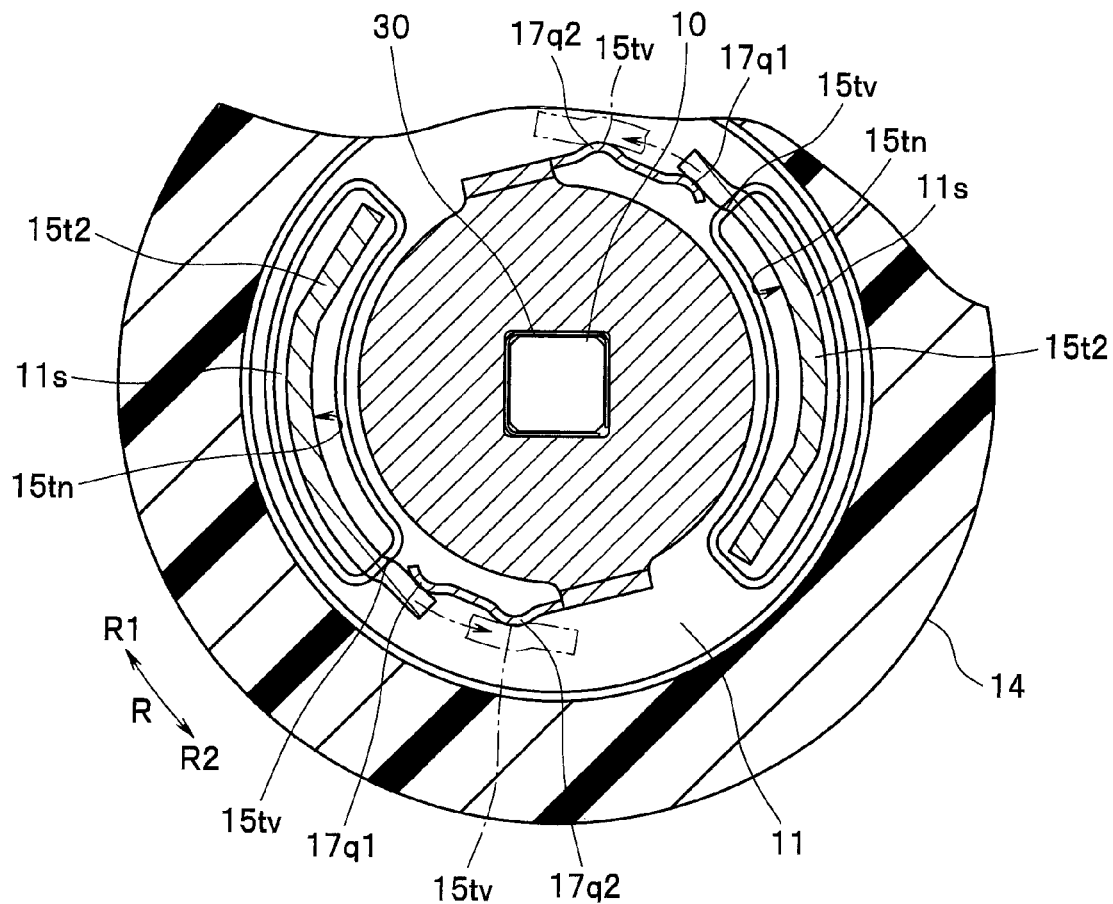
FIG. 11 is a partial sectional view of the bending operation apparatus taken along the XI-XI line in FIG. 2.
Figure 12:
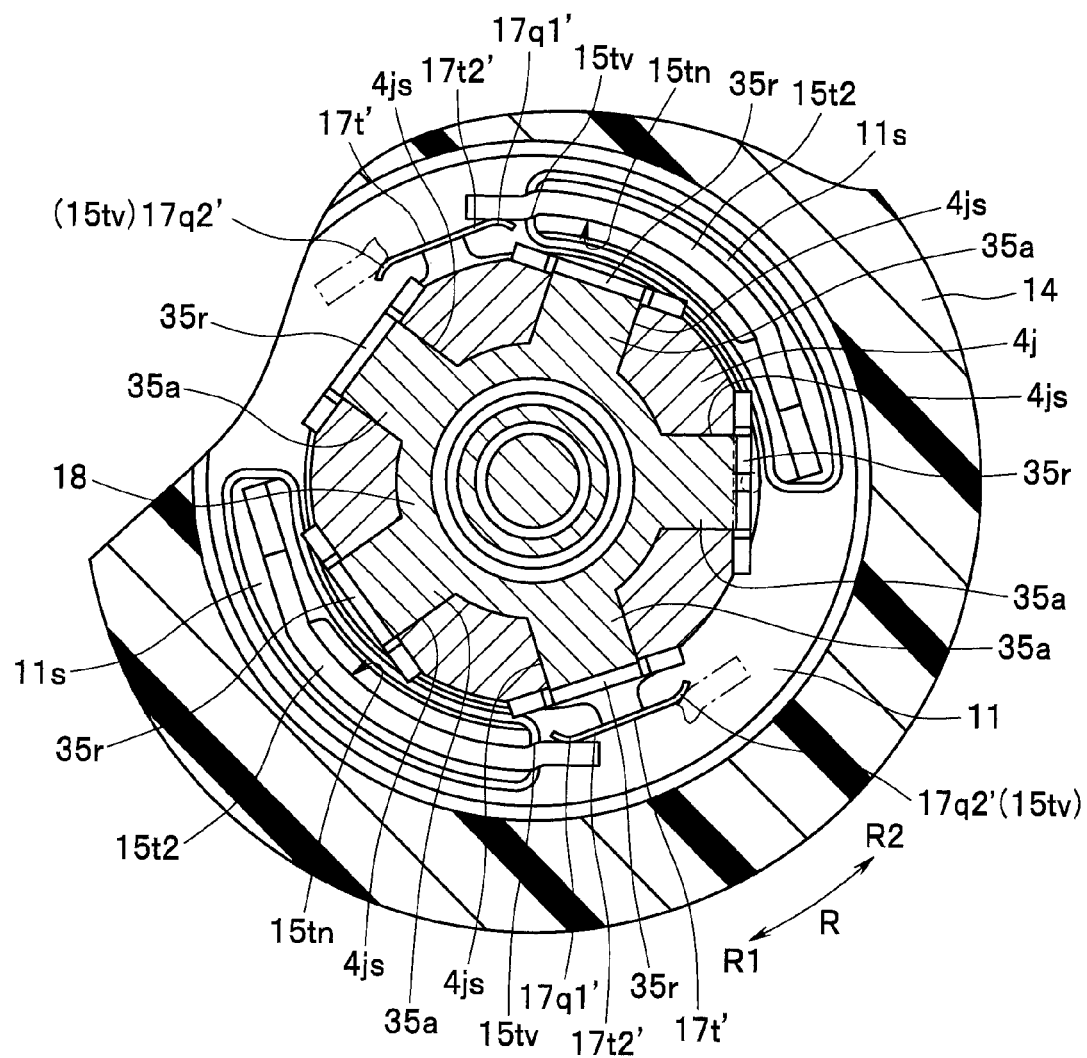
FIG. 12 is a partial sectional view of the bending operation apparatus taken along the XII-XII line in FIG. 2.
Figure 13:
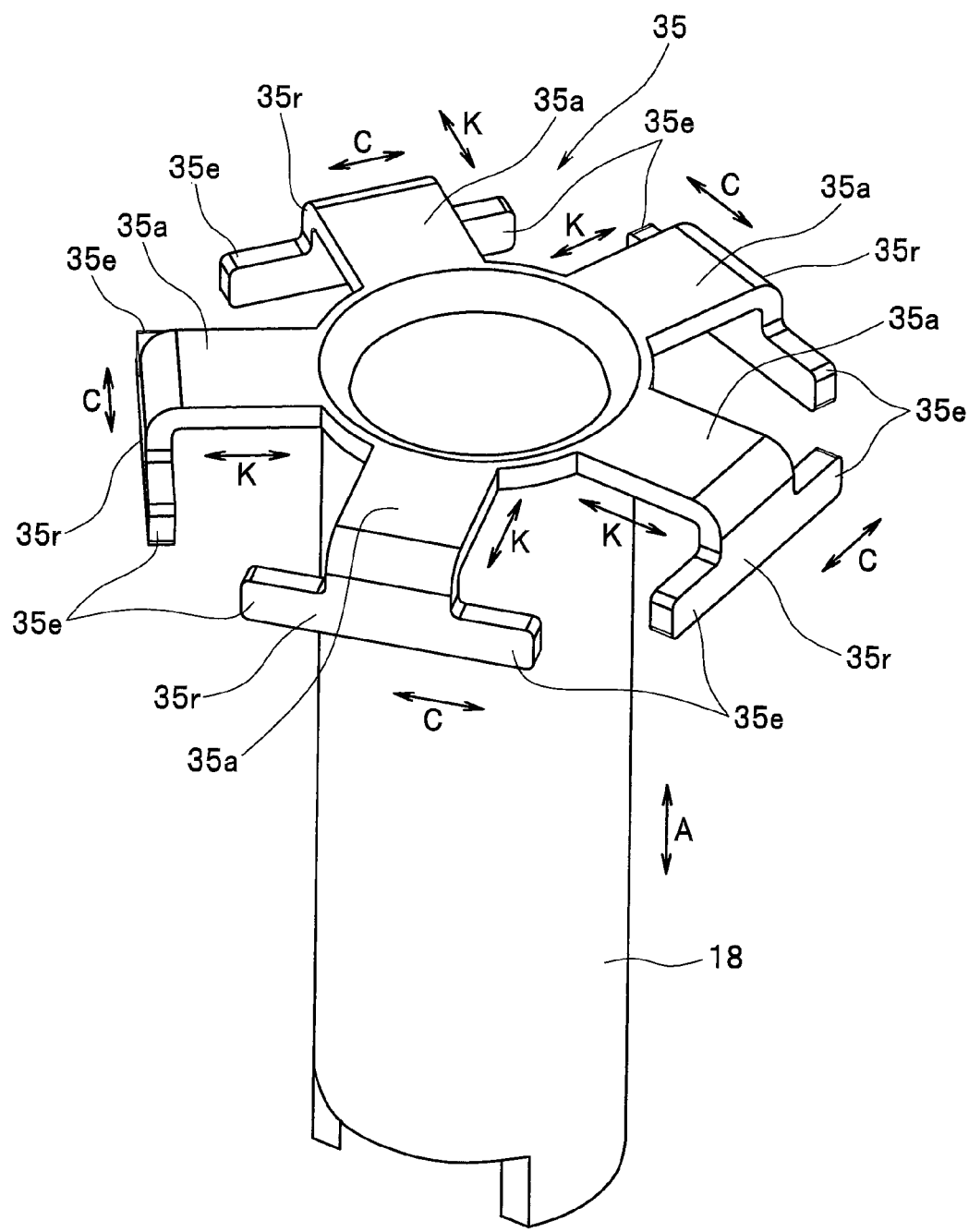
FIG. 13 is a perspective view showing a rotation shaft of FIG. 4 under enlargement.

Further, FIG. 11 is a partial sectional view of the bending operation apparatus taken along the XI-XI line in FIG. 2. FIG. 12 is a partial sectional view of the bending operation apparatus taken along the XII-XII line in FIG. 2. FIG. 13 is a perspective view showing a rotation shaft of FIG. 4 under enlargement.

Figure 14:
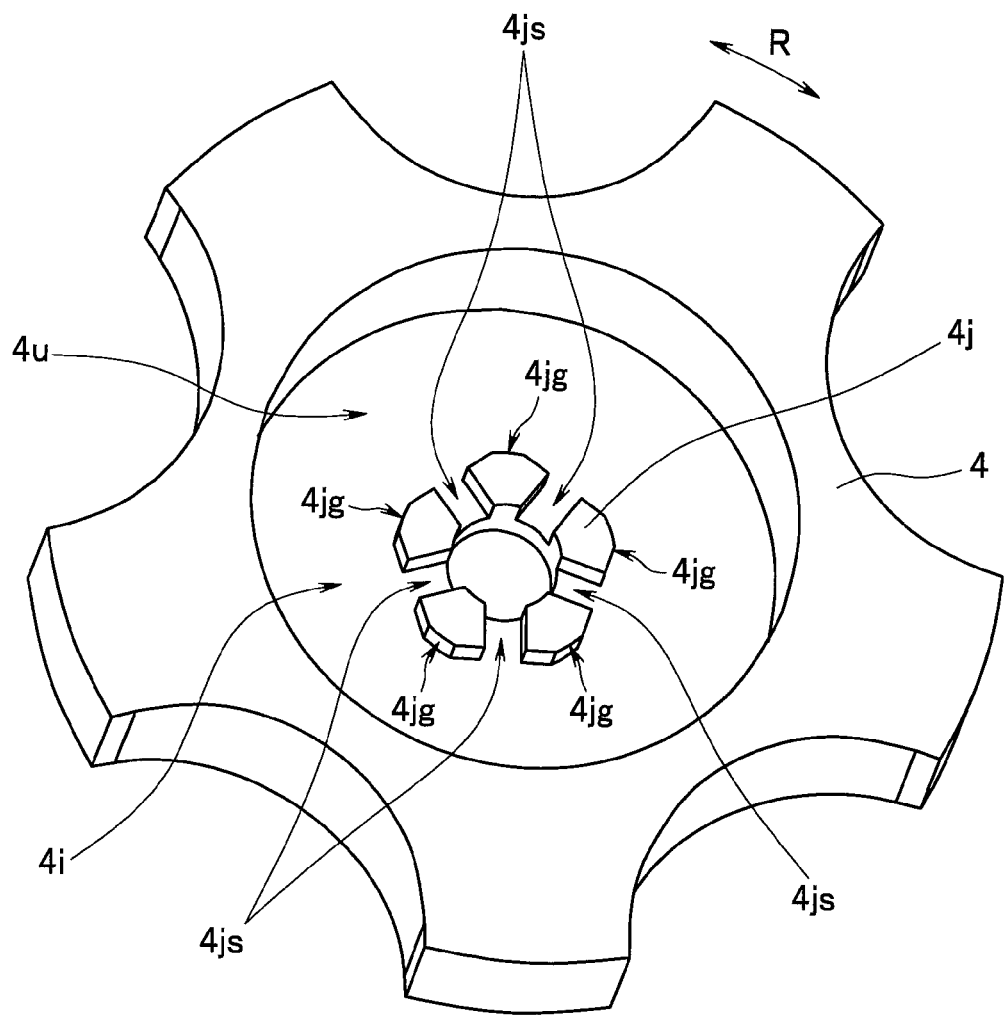
FIG. 14 is an enlarged perspective view of a bending operation knob of FIG. 4 seen from the XIV direction in FIG. 4.
Figure 15:
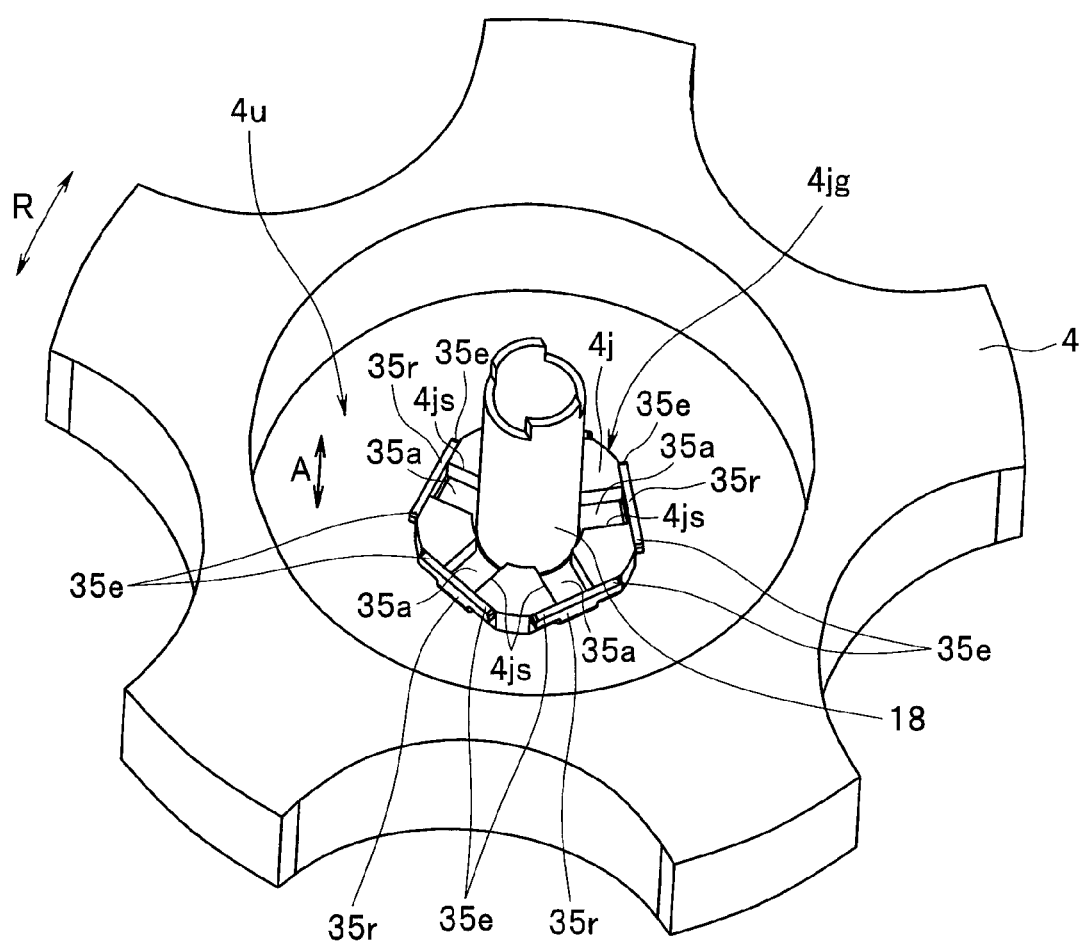
FIG. 15 is a perspective view showing a state in which a holding portion of the rotation shaft is locked to a portion to be engaged of the bending operation knob of FIG. 14.

Furthermore, FIG. 14 is an enlarged perspective view of the bending operation knob of FIG. 4 seen from the XIV direction in FIG. 4. FIG. 15 is a perspective view showing a state in which a holding portion of the rotation shaft is locked to a portion to be engaged of the bending operation knob of FIG. 14.

Figure 16:
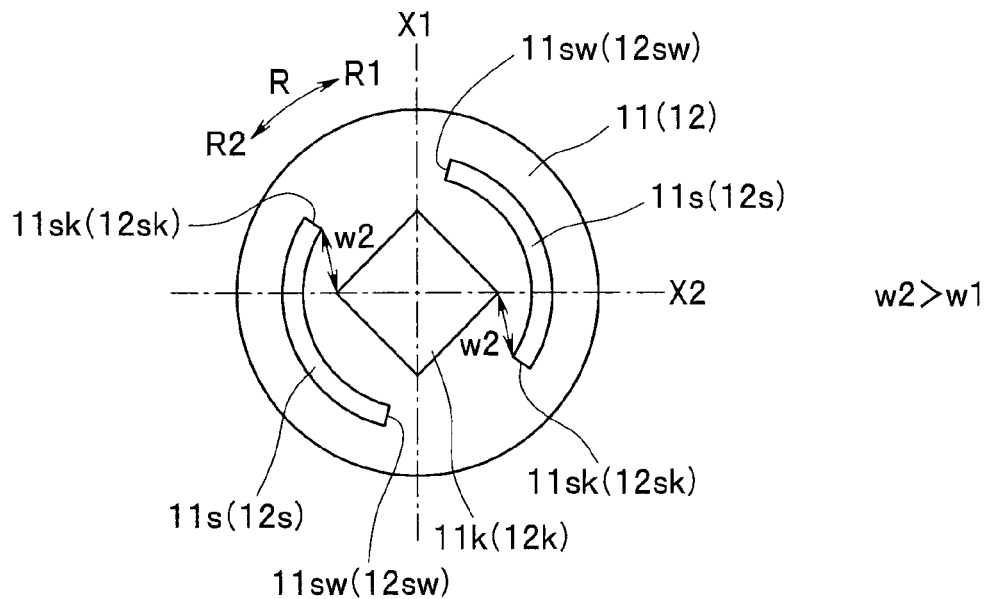
FIG. 16 is a plan view schematically showing the movable disk of FIG. 4.
Figure 17:
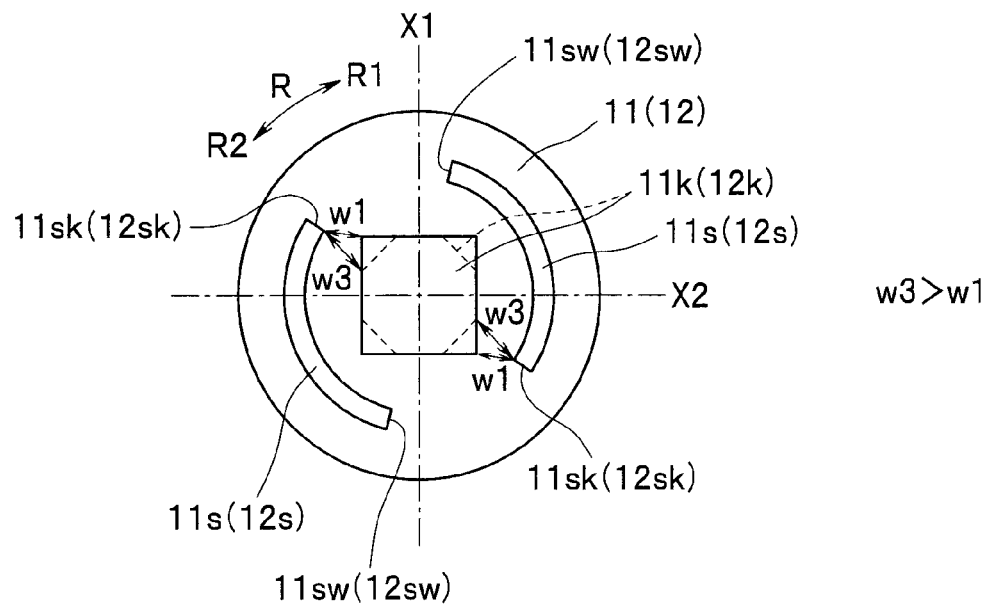
FIG. 17 is a plan view of the movable disk showing a conventional disposition position of a hole formed in each of the two movable disks, along with a shape of a hole of a modification.

Further, FIG. 16 is a plan view schematically showing the movable disk of FIG. 4. FIG. 17 is a plan view of the movable disk showing a conventional disposition position of a hole formed in each of the two movable disks, along with a shape of a hole of a modification.

Figure 18:
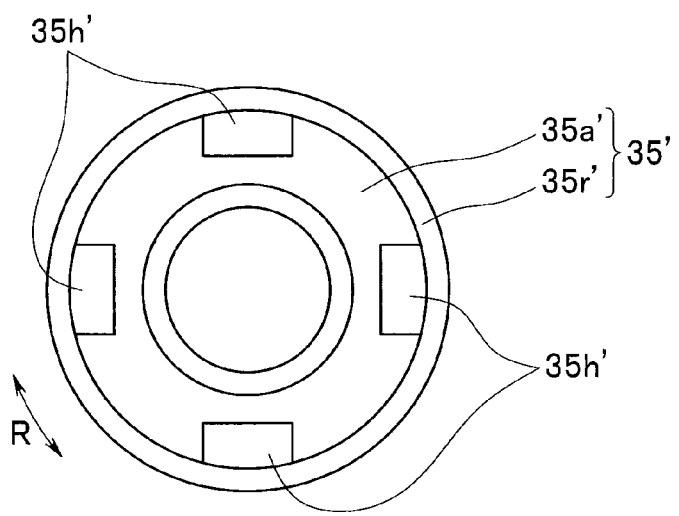
FIG. 18 is a plan view showing a modification of a shape of the holding portion of the rotation shaft of FIG. 4 from an operation portion side.
Figure 19:
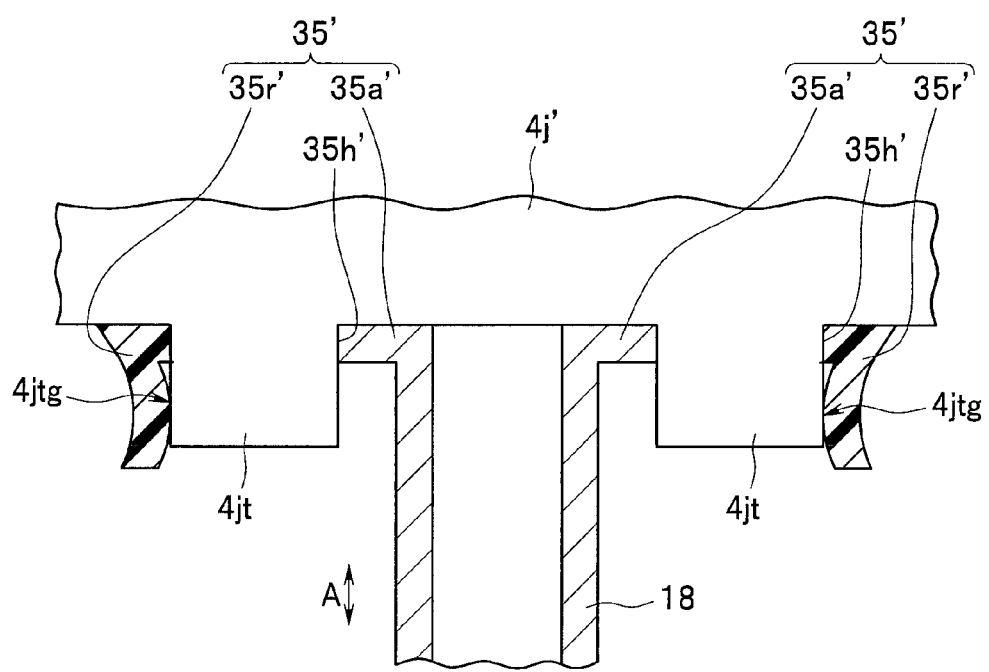
FIG. 19 is a partial sectional view schematically showing a state in which the portion to be engaged of the bending operation knob is locked to the holding portion of FIG. 18.

Furthermore, FIG. 18 is a plan view showing a modification of a shape of the holding portion of the rotation shaft of FIG. 4 from an operation portion side. FIG. 19 is a partial sectional view schematically showing a state in which the portion to be engaged of the bending operation knob is locked to the holding portion of FIG. 18.

Note that in the configuration of the bending operation apparatus 100 shown as follows, a configuration relating to the bending operation knob 4 and the fixing lever 5 will be shown as an example.

As shown in FIG. 2, the bending operation knob 4 is locked in an unfixed state to an end portion (hereinafter, called an upper end) that is separated from the operation portion 3 in an axial direction A of a cylindrical rotation shaft 18 provided by being extended along the axial direction A that is a direction substantially orthogonal to the insertion direction S from an inside of the operation portion 3, and is rotatable in a direction R1 or a direction R2 (for both of them, refer to FIG. 4) in a rotational direction R, with the rotation shaft 18.

More specifically, as shown in FIG. 14, in a rotation center of the bending operation knob 4 that is on a top surface 4u configuring an inner surface of the bending operation knob 4, a convex portion 4j that is a portion to be engaged protruding to an operation portion 3 side in a clearance 4i in an inside of the bending operation knob 4 is formed. In the convex portion 4j, a plurality of, for example, five slits 4js are radially formed from the rotation center of the bending operation knob 4 in a diameter direction of the convex portion 4j by having predetermined spaces in the rotational direction R.

Further, as shown in FIG. 2, FIG. 4 and FIG. 13, a holding portion 35 is integrally formed at the upper end of the rotation shaft 18. Note that the holding portion 35 may be formed to be a separate body from the rotation shaft 18 and may be separable from the upper end of the rotation shaft 18, but the configuration additionally requires a structure that fixes the holding portion 35 to the upper end of the rotation shaft 18, and therefore, is not preferable.

As shown in FIG. 13, the holding portion 35 has a main part configured by including arm portions 35a that are at least three, for example, five engaging portions that radially extend in a diameter direction K of the rotation shaft 18 from the upper end of the rotation shaft 18, and folded portions 35r that are folded in a direction parallel to the rotation shaft 18, namely, a direction parallel to the shaft direction A continuously with respect to the respective arm portions 35a from extended ends in the diameter direction K of the arm portions 35a.

The five arm portions 35a are engaged with the five slits 4js of the convex portion 4j in a fixed state as shown in FIG. 12 and FIG. 15. Therefore, in the holding portion 35, the arm portions 35a are formed in positions, shapes and the number that allow the arm portions 35a to engage with the slits 4js. That is, the number of arm portions 35a needs to be the same as the number of slits 4js.

Further, a plate thickness in the axial direction A of the arm portion 35a is formed to be smaller than a depth in the axial direction A of the slit 4js. Further, by engagement (fitting) of the respective arm portions 35a into the respective slits 4js, positioning in the rotational direction R of the bending operation knob 4 to the holding portion 35 is performed.

The five folded portions 35r abut on an outer circumferential face 4jg of the convex portion 4j from a plurality of directions in the diameter direction K as shown in FIG. 2 and FIG. 15, when the arm portions 35a are engaged with the slits 4js.

Further, as shown in FIG. 13, the respective folded portions 35r further include extending sites 35e that extend along a direction C orthogonal to the two directions of the axial direction A and the diameter direction K, and as shown in FIG. 15, the extending sites 35e also abut on the outer circumferential face 4jg of the convex portion 4j from a plurality of directions in the diameter direction K.

Note that the folded portions 35r and the extending sites 35e abut on the outer circumferential face 4jg of the convex portion 4j from a plurality of directions in the diameter direction, whereby fitting unsteadiness of the bending operation knob 4 to the upper end of the rotation shaft 18 is prevented even in an unfixed state. That is, the bending operation knob 4 is prevented from being inclinedly assembled to the upper end of the rotation shaft 18.

This is because even if the bending operation knob 4 is to be inclined with respect to the upper end of the rotation shaft 18, the bending operation knob 4 cannot be inclined since the folded portions 35r and the extending sites 35e abut on the outer circumferential face 4jg of the convex portion 4j from a plurality of directions.

Furthermore, when the arm portions 35a are engaged with the slits 4js, a space a1 between lower ends at the operation portion 3 side in the axial direction A of the respective folded portions 35r and the respective extending sites 35e, and a base portion 17b of a resistance giving member 17, which will be described later, located in the clearance 4i in the inside of the bending operation knob 4 is formed to be shorter than a length a2 (a1<a2) in the axial direction A of the folded portion 35r.

In regard with the above, when the bending operation knob 4 with the rotation shaft 18 is distributed as a unit, if the rotation shaft 18 is in an unfixed state to the bending operation knob 4, the rotation shaft 18 is usually detached from the bending operation knob 4. However, in the present configuration, a1<a2 is satisfied, and therefore, even if the lower end of the rotation shaft 18 is directed to the underside, the arm portions 35a are located in the slits 4js in a state in which the lower ends of the folded portions 35r and the extending sites 35e abut on the base portion 17b. Therefore, the arm portions 35a are not disengaged in the axial direction A from the slits 4js, and therefore, handling as the unit is facilitated.

From the above, the upper end of the rotation shaft 18 is locked to the top surface 4u of the bending operation knob 4 by the respective arm portions 35a of the holding portion 35 formed at the upper end of the rotation shaft 18 engaging with the respective slits 4js of the convex portion 4j formed on the top surface 4u in an unfixed state, and the respective folded portions 35r and by the extending sites 35e of the holding portion 35 abutting onto the outer circumferential face 4jg of the convex portion 4j from a plurality of directions in the diameter direction K.

Note that the shape of the holding portion 35 is not limited to the one shown in FIG. 2, FIG. 4 and FIG. 13. For example, as shown in FIG. 18 and FIG. 19, a holding portion 35' may be configured by an arm portion 35a' that extends to an outer side in a diameter direction from the upper end of the rotation shaft 18, and has a shape seen in a plan view from the axial direction A being a ring shape, and a folded portion 35r' that continues from an outer circumferential edge of the arm portion 35a' and is folded along the axial direction A toward the operation portion 3 side.

As shown in FIG. 19, a plurality of protruding portions 4jt that extend to the operation portion 3 side along the axial direction A are formed on a convex portion 4j' that is a portion to be engaged and formed on the top surface 4u of the bending operation knob 4.

A plurality of, for example, four hole portions 35h' that are engaging portions penetrating in the axial direction A are formed in the circular arm portion 35a'. Note that the hole portion 35h' is a hole in which the protruding portion 4jt is engaged when the holding portion 35 is engaged with the convex portion 4j', and the same number of hole portions 35h' as that of the protruding portions 4jt are formed.

The folded portion 35r' abuts onto the outer circumferential face 4jtg of the protruding portion 4jt with an elastic force when the respective protruding portions 4jt are engaged with the respective hole portions 35h', and prevents fitting unsteadiness of the bending operation knob 4 with respect to the upper end of the rotation shaft 18 even in an unfixed state by abutment onto the protruding portions 4jt from a plurality of directions in the diameter direction K.

With these configurations shown in FIG. 18 and FIG. 19, a similar effect to the holding portion shown in FIG. 13 can be obtained. Note that the shape of the holding portion 35 is not limited to the one described above, and may be in any shape as long as the holding portion 35 is configured such that the folded portions abut on an outer circumferential face of the engaging portion from a plurality of directions in the diameter direction K in a state in which the engaging portion is engaged with the portion to be engaged.

Further, returning to FIG. 2, an end portion (hereinafter, called a lower end) in the axial direction A that is located in the inside of the operation portion 3 of the rotation shaft 18 is fitted to a sprocket 19 that is provided in the inside of the operation portion 3. Note that a chain (not illustrated) that causes the bending portion 2w to bend is wound around the sprocket 19.

Thereby, when the bending operation knob 4 is rotationally operated in the direction R1 or the direction R2, the rotation shaft 18 that is locked to the bending operation knob 4 in an unfixed state by the aforementioned configuration is also rotated in the same direction as the bending operation knob 4, and the sprocket 19 is also rotated in the same direction, so that any one of the sides of the chain is pulled, and thereby the bending portion 2w bends in any one of the up and the down directions.

Note that the configuration is not limited to the combination of the sprocket 19 and the chain, but may be a configuration in which the lower end of the rotation shaft 18 is fitted to a pulley, and a wire that is wound around the pulley is pulled with rotation of the pulley.

At an outer periphery in the diameter direction of the rotation shaft 18, a cylindrical fixed shaft 10 that extends along the axial direction A from the inside of the operation portion 3 is provided in such a manner that an end portion (hereinafter, called an upper end) side that separates from the operation portion 3 is inserted through the clearance 4i in the inside of the bending operation knob 4. Note that the fixed shaft 10 is formed along the axial direction A in such a manner that a sectional shape in the insertion direction S orthogonal to the axial direction A is a polygonal shape, for example, a rectangular shape.

Note that the fixed shaft 10 is fixed to a sheathing member 3g of the operation portion 3 via an O-ring or the like, and is located on the same axis with a predetermined space in the diameter direction with respect to the rotation shaft 18, and thereby the fixed shaft 10 is irrotational with respect to the rotation shaft 18.

Further, on an outer periphery of the fixed shaft 10, the fixing lever 5 that is located in the clearance 4i in the inside of the bending operation knob 4 and is formed from, for example, a resin is caused to abut rotatably in the rotational direction R via an O-ring 21 and the like.

More specifically, as shown in FIG. 4 and FIG. 5, an inner circumferential face of a ring-shaped portion 5b of the fixing lever 5 that is configured by a grasping portion 5r and the ring-shaped portion 5b is caused to abut on the outer periphery of the fixed shaft 10 rotatably in the rotational direction R via the O-ring 21 or the like.

On an outer periphery of the ring-shaped portion 5b of the fixing lever 5, an inner circumferential face of a support plate 23 that is located in the clearance 4i in the inside of the bending operation knob 4 is caused to abut via an O-ring 22 or the like. Note that an outer circumferential face of the support plate 23 is caused to abut on an inner circumferential face 4n of the bending operation knob 4 via an O-ring 24 or the like.

Furthermore, in the outer periphery of the fixed shaft 10, at a top surface 4u side from the ring-shaped portion 5b of the fixing lever 5, a cam member 15 that is located in the clearance 4i in the inside of the bending operation knob 4, and is formed from, for example, a metal is located on the same axis as the fixing lever 5 in the axial direction A.

As shown in FIG. 4, the cam member 15 has a main part configured by including a ring-shaped base portion 15b, and two protruding portions 15t that protrude each in an inverted-L-shape to the top surface 4u side in the axial direction A respectively from the base portion 15b in such a manner as to face each other with respect to the axial direction A.

Further, as shown in FIG. 4, a plurality of convex portions 15p protruding in an inner circumferential direction in a diameter direction from the base portion 15b are respectively fitted in a plurality of concave portions 5m that are formed on a surface at a cam member 15 side, of the ring-shaped portion 5b of the fixing lever 5, whereby the cam member 15 is fixed to the fixing lever 5.

That is, the cam member 15 is made rotatable in the direction R1 or the direction R2 in the rotational direction R together with the fixing lever 5 by fitting of the convex portions 15p into the concave portions 5m. In other words, the fixing lever 5 performs a rotational operation of the cam member 15.

As shown in FIG. 7, the protruding portion 15t of the cam member 15 has a main part configured by including a raised site 15t1 that protrudes to the top surface 4u side in the axial direction A, a transverse site 15t2 that is extended in a circular arc shape along the rotational direction R to the direction R2 from a protruding end of the raised site 15t1, and a step portion 15t3 that is located at a direction R1 side, of the raised site 15t1.

Note that the raised site 15t1 of the protruding portion 15t is stronger against a force that acts from the axial direction A to the cam member 15 as a length of the raised site in the axial direction A is longer. That is, the cam member 15 becomes strong against deformation in the axial direction A.

From the above, if the cam member 15 is provided with the raised site 15t1, strength against the force that is applied from the axial direction A is given. Therefore, the base portion 15b does not have to be formed to be thick and the cam member does not have to be large in diameter in the diameter direction as in the conventional apparatus.

From the above, not only a thickness in the axial direction A of the base portion 15b can be made small, but also the diameter of the cam member 15 in the diameter direction can be made small, and therefore, contribution is made to reduction in weight and miniaturization of the bending operation apparatus 100.

Further, as shown in FIG. 5 to FIG. 7, in the protruding portion 15t, between the base portion 15b and the transverse site 15t2 in the axial direction A, a cam groove 15c is formed along the rotational direction R.

As shown in FIG. 5, the cam groove 15c is formed by having an inclined surface or a circular-arc shaped surface so that a groove space in the axial direction A becomes m1 that is smaller than m2 (m2>m1) from the m2 toward the direction R1.

Furthermore, as shown in FIG. 7, an extended end at a direction R2 side, of the transverse site 15t2 of the protruding portion 15t is bent in a crank shape, whereby a step portion 15tv is formed on an inner circumferential face 15tn of the transverse site 15t2.

Returning to FIG. 2, to the top surface 4u side from the base portion 15b of the cam member 15, in the outer periphery of the fixed shaft 10, one movable disk 11 and the other movable disk 12 that are located on the same axis as the cam member 15 in the axial direction A, are located in the clearance 4i in the inside of the bending operation knob 4, and are formed from, for example, a metal are respectively fixed. Note that the movable disk 11 and the movable disk 12 are formed into the same shape and in the same size.

More specifically, in the movable disks 11 and 12, through-holes 11k and 12k that penetrate in the axial direction A that have outer shapes substantially equal to the outer shape of the fixed shaft 10, and have shapes seen in a plan view from the top surface 4u side being polygonal shapes, for example, rectangular shapes are formed, and the movable disks 11 and 12 are fixed to the fixed shaft 10 that is inserted through the through-holes 11k and 12k.

Note that a position of the through-hole 11k of the movable disk 11 is formed in the same position as the position of the through-hole 12k of the movable disk 12. That is, when the movable disk 11 and the movable disk 12 are superimposed on each other, the respective through-holes 11k and 12k are superposed on each other.

Thus, the movable disks 11 and 12 are fixed to the fixed shaft 10, and therefore, configured to be irrotational with respect to the rotation shaft 18, together with the fixed shaft 10.

Note that as shown in FIG. 2, a positioning spring 30 that has a predetermined length in the axial direction A is fitted in between the respective through-holes 11k and 12k, and the outer periphery of the fixed shaft 10.

More specifically, as shown in FIG. 8, the positioning spring 30 includes a shaft member 30v that is formed into a cylindrical shape by an elongated plate shaped member having a predetermined length, for example, being folded at 90° three times with predetermined spaces, and has a predetermined length in the axial direction A.

Note that the shaft member 30v is covered for the outer periphery of the fixed shaft 10 as shown in FIG. 2. Therefore, when the fixed shaft 10 is formed into a polygonal shape other than a rectangular shape, the shaft member 30v is accordingly formed by being folded into the same external shape as that of the fixed shaft.

Further, as shown in FIG. 2, the shaft member 30v is formed to have such a length as to penetrate through at least both of the through-holes 11k and 12k in the axial direction A. That is, the shaft member 30v is formed to have such a length that in the axial direction A, an upper end of the shaft member 30v protrudes to the top surface 4u side from a top surface of the movable disk 11, and a lower end protrudes to the operation portion 3 side from a bottom surface of the movable disk 12.

The shaft member 30v performs positioning in the rotational direction R of the movable disk 12 to the movable disk 11 by being inserted through insides of the respective through-holes 11k and 12k.

This is because in the configuration that moves the two movable disks 11 and 12 with use of the cam member 15, the problem arises that positioning in the rotational direction R of the other movable disk 12 to the one movable disk 11 is difficult at the time of assembly. More specifically, when the two movable disks 11 and 12 are fitted onto the fixed shaft 10, the problem arises that positioning of the through-holes 11k and 12k of the movable disks 11 and 12 to the fixed shaft 10 is difficult.

Therefore, if the shaft member 30v is inserted through the through-holes 11k and 12k before the movable disks 11 and 12 are assembled to the fixed shaft 10 as in the present configuration, the advantage is brought about that positioning in the rotational direction R of the movable disk 12 to the movable disk 11 can be easily performed, and positioning of the through-holes 11k and 12k of the movable disks 11 and 12 to the fixed shaft 10 can be performed.

Note that a stopper that prevents the shaft member 30v from being detached from the through-holes 11k and 12k to the operation portion 3 side may be formed at a lower end at the operation portion 3 side, of the shaft member 30v.

Further, as shown in FIG. 8, on four outer peripheral surfaces of the shaft member 30v, claw portions 30t that protrude to an outer side in the diameter direction K of the shaft member 30v, and are elastically deformable in the diameter direction K are formed, for a gap between the movable disk 11 and the movable disk 12 in the axial direction A, in a state in which the shaft member 30v is inserted through the through-holes 11k and 12k.

The claw portion 30t causes the movable disk 11 to move to the first position from the second position by an elastic force and keep the first position, when the fixing lever 5 is rotated in the direction R1, and thereby releases fixation of the bending operation knob 4, and the cam member 15 is rotated in the direction R1, as will be described later.

Further, when the movable disk 11 is caused to move to the second position from the first position, the claw portion 30t retracts to an inner side in the diameter direction K by the through-hole 11k of the movable disk 11, and is located in the through-hole 11k, as will be described later.

Note that the configuration of the positioning spring 30 as above is also applied to the two movable disks located in the bending operation knob 6.

Returning to FIG. 2, between the two movable disks 11 and 12 in the axial direction A, a fixed disk 14 that is located on the same axis in the axial direction A as the two movable disks 11 and 12, located in the clearance 4i in the inside of the bending operation knob 4, and is formed from, for example, a resin is provided.

The fixed disk 14 has an O-ring 25 that is provided on an outer circumferential face thereof and that abuts on the inner circumferential face 4*n* of the bending operation knob 4 with a shape and a pressing amount set in advance so as to generate a proper bending holding force for the bending operation knob 4, and has a flange portion 14*f* that is sandwiched by the two movable disks 11 and 12 in the axial direction A, in the second position (see FIG. 6), which will be described later.

Note that the O-ring 25 may discontinuously abut on the inner circumferential face 4*n*. Further, the fixed disk 14 rotates with the bending operation knob 4 in the first position (see FIG. 5), which will be described later.

Further, as shown in FIG. 4, in the movable disks 11 and 12, at a predetermined superposed position in a state in which the movable disks 11 and 12 are seen in a plan view from, for example, the top surface 4*u* side in the axial direction A, two slits 11*s* and two slits 12*s* having partial circular arc shapes in the rotational direction R are respectively formed for the respective disks 11 and 12 so as to penetrate in the axial direction A, to be thereby symmetrical about a rotation center of the rotation shaft 18 and partially surround the respective through-holes 11*k* and 12*k*.

Note that positions of the slits 11*s* of the movable disk 11 are formed in the same positions as positions of the slits 12*s* of the movable disk 12. That is, when the movable disk 11 and the movable disk 12 are superimposed on each other, the respective slits 11*s* and 12*s* are superposed on each other.

The protruding portions 15*t* of the cam member 15 are penetrated through the respective slits 11*s* and 12*s* to be movable in the direction R1 or the direction R2 in the rotational direction R separately from the rotation shaft 18. That is, in a state in which the protruding portions 15*t* of the cam member 15 are penetrated through the respective slits 11*s* and 12*s*, parts of the two movable disks 11 and 12 are fitted in the cam groove 15*c*.

Note that the protruding portion 15*t* is movable in the rotational direction R in the slits 11*s* and 12*s* in a position where the step portion 15*t*3 abuts on an opening end portion 12*sk*, and a position where end portions 11*sw* and 12*sw* (see FIG. 5 and FIG. 6) of the two movable disks 11 and 12 abut on an end portion 15*ct* of the cam groove 15*c*.

Further, when the step portion 15*t*3 abuts on the opening end portion 12*sk*, the two movable disks 11 and 12 are separated by having the first space d1 therebetween in the axial direction A as shown in FIG. 5 by the claw portions 30*t* (see FIG. 8), which will be described later, of the aforementioned positioning spring 30. Note that hereinafter, the position in which the movable disks 11 and 12 are separated at the first space d1 in the axial direction A will be called the first position.

Further, in the first position, a distal end side in the direction R2 of the transverse site 15*t*2 abuts on a top surface of the movable disk 11, and therefore, the protruding portion 15*t* is not detached from the respective slits 11*s* and 12*s* to the operation portion 3 side.

Furthermore, when the step portion 15*t*3 of the protruding portion 15*t* of the cam member 15 abuts on the opening end portion 12*sk* in the first position shown in FIG. 5, the protruding portion 15*t* of the cam member 15 is restrained from rotating in the direction R1 with respect to the slit 12*s*.

Here, as described above, it is indicated that the cam groove 15*c* is formed in the rotational direction R in the protruding portion 15*t*.

When the cam member 15 is rotated in the direction R2 from the first position, the protruding portion 15*t* moves to the direction R2 in the slits 11*s* and 12*s*, until the end portions 11*sw* and 12*sw* of the slits 11*s* and 12*s* of the movable disks 11 and 12 abut on the end portion 15*ct* in the rotational direction R of the cam groove 15*c*. By the movement, the movable disk 11 is guided by the inclined surface or the circular-arc shaped surface formed on the cam groove 15*c*, and the rotational force is converted into the force in the axial direction A, whereby the movable disk 11 moves to the second position where the movable disk 11 is separated by having the second space d2 (d2<d1) that is shorter than the first space d1 in the axial direction A, with respect to the movable disk 12, as shown in FIG. 6.

Namely, the cam groove 15*c* has a shape that moves the movable disk 11 to the second position from the first position along with rotation of the cam member 15 in the direction R2, and has a function of converting the rotational force into the force in the axial direction A and causing the movable disk 11 to move to the second position from the first position, along with rotation of the cam member 15 in the direction R2.

Note that the cam groove 15*c* may be formed into a shape that moves not only the movable disk 11 but also both the movable disks 11 and 12 to the second position from the first position.

Further, at this time, the claw portion 30*t* of the positioning spring 30 retracts into an inner side in the diameter direction K by the through-hole 11*k* of the movable disk 11, and is located in the through-hole 11*k* in the second position.

Further, in the second position shown in FIG. 6, the flange portion 14*f* of the fixed disk 14 is sandwiched by the movable disks 11 and 12, whereby rotation of the fixed disk 14 that rotates with the bending operation knob 4 is fixed, and the O-ring 25 abuts onto the inner circumferential face 4*n* of the bending operation knob 4 with a frictional force. By the frictional force, a rotation position of the bending operation knob 4 is fixed. Note that at this time, the force that sandwiches the flange portion 14*f* by the movable disks 11 and 12 is larger than the frictional force produced by the bending operation knob 4 and the O-ring 25.

Further, when the cam member 15 is rotated in the direction R1 opposite to the direction R2 in the second position shown in FIG. 6, the protruding portion 15*t* moves in the slits 11*s* and 12*s* until the step portion 15*t*3 abuts on the opening end portion 12*sk* of the slit 12*s*, and in this case, the movable disk 11 is caused to move to the first position shown in FIG. 5 by the elastic force of the claw portion 30*t* (see FIG. 8) of the aforementioned positioning spring 30 instead of the shape of the cam groove 15*c*.

In the above state, the flange portion 14*f* is not sandwiched by the movable disks 11 and 12, the bending operation knob 4 and the fixed disk 14 are rotatable.

From the above, in the clearance 4*i* in the inside of the bending operation knob 4, the movable disks 11 and 12 are movable to the first position where the movable disks 11 and 12 are separated by having the first space d1, and the second position where the movable disks 11 and 12 are separated by having the second space d2, in the axial direction A, along with rotation of the fixing lever 5.

Here, it is indicated that in the movable disks 11 and 12 formed into the same shape and the same size, the slits 11*s* and 12*s*, and the rectangular through-holes 11*k* and 12*k* that penetrate in the axial direction A are formed, as described above.

However, if the through-holes 11*k* and 12*k* are opened in such an orientation that the respective sides of the through-holes 11*k* and 12*k* the shapes, when seen in a plan view, of which are rectangular shapes are parallel to two axes x1 and x2 that pass through the rotation center of the rotation shaft 18 and perpendicularly intersect each other in the planar direction (the diameter direction) of the movable disks 11 and 12, as shown in FIG. 17, in the state in which the respective movable disks 11 and 12 are seen in a plan view from the axial direction A, a width w1 of a wall in the planar direction between each of the corner portions of the through-holes 11k and 12k and each of the end portions 11sk and 12sk of the slits 11s and 12s cannot be sufficiently secured.

Note that the respective end portions 11sk and 12sk of the slits 11s and 12s are positions to which force is applied the most in the slits 11s and 12s, with abutment of the step portion 15t3 of the protruding portion 15t in the slits 11s and 12s as described above, and therefore, if the width of the wall in the diameter direction between each of the end portions 11sk and 12sk of the slits 11s and 12s and each of the corner portions of the through-holes 11k and 12k cannot be sufficiently secured, the problem arises that strength of the portions is reduced.

Therefore, in the conventional apparatus, the strength of the aforementioned portions is secured by the width of the wall in the axial direction A being ensured to be large, or the width of the wall in the diameter direction being ensured by the diameters of the movable disks 11 and 12 in the diameter direction being increased, but this is not preferable because the movable disks 11 and 12 are increased in wall thickness in the axial direction A and increased in diameter in the diameter direction.

Therefore, in the present embodiment, the through-holes 11k and 12k are penetrated in positions where the respective rectangular through-holes 11k and 12k are rotated by 45° in the rotational direction R from those in FIG. 17, namely, in orientations in which the corner portions of the respective through-holes 11k and 12k correspond to the axes x1 and x2, as shown in FIG. 16.

From the above, as shown in FIG. 16, without the movable disks 11 and 12 being increased in wall thickness in the axial direction A or increased in diameter in the diameter direction, a width w2 of the wall in the diameter direction between each of the corner portions of the respective rectangular through-holes 11k and 12k and each of the end portions 11sk and 12sk of the slits 11s and 12s can be ensured to be larger than the width w1 of the wall shown in FIG. 17 (w1<w2).

Note that if the planar shapes of the through-holes 11k and 12k are made, for example, hexagonal shapes as shown by the dotted lines in FIG. 17, widths w3 of the walls between corner portions of the hexagonal shapes and the end portions 11sk and 12sk can be ensured to be larger than the width w1 of the conventional walls (w1<w3).

Returning to FIG. 2, in the outer periphery of the fixed shaft 10, the resistance giving member 17 that is located in the clearance 4i in the inside of the bending operation knob 4 is fixed to an inner side in the diameter direction from the protruding portion 15t of the cam member 15 as shown in FIG. 2 and FIG. 10, at the top surface 4u side from the movable disk 11.

The resistance giving member 17 prevents unintentional movement of the cam member 15 in the second position to the direction R1 by giving the resistance force to the rotation of the cam member 15. Further, the resistance giving member 17 is an irrotational member similarly to the fixed shaft 10.

As shown in FIG. 9, the resistance giving member 17 has a main part configured by having a base portion 17b having a through-hole 17k, with a shape seen in a plan view from the axial direction A being a rectangular shape, fixed to the fixed shaft 10, and rocking portions 17t that are raised each in an inverted-L shape to the top surface 4u side in the axial direction A from an outer circumferential edge of the base portion 17b so as to be symmetrical with respect to the rotation center of the rotation shaft 18.

The rocking portion 17t has a main part configured by including a raised site 17t1 raised in the axial direction A from an outer circumferential edge portion of the base portion 17b, and a transverse site 17t2 that is extended to be elongated to the direction R1 side along the rotational direction R from a raised end of the raised site 17t1.

As shown in FIG. 10 to FIG. 12, the rocking portion 17t fixes the rotation position of the cam member 15 in the second position by an outer circumferential face of the transverse site 17t2 abutting onto the inner circumferential face 15tn of the transverse site 15t2 of the protruding portion 15t with an urging force, and the rocking portion 17t is configured by an elastic member rockable in the diameter direction.

More specifically, as shown in FIG. 9 to FIG. 11, in the rocking portion 17t, two convex portions 17q1 and 17q2 are formed to be separated in the rotational direction R at positions at an end portion in the direction R1 side and at a raised site 17t1 side, in the outer circumferential face of the transverse site 17t2, and the two convex portions 17q1 and 17q2 abut onto the inner circumferential face 15tn with an urging force.

The convex portion 17q1 abuts on the inner circumferential face 15tn of the transverse site 15t2 of the cam member 15, and is fitted in the step portion 15tv formed on the inner circumferential face 15tn with movement of the cam member 15 in the direction R2, whereby the convex portion 17q1 gives click sensing to an operator of the fixing lever 5, and thereby notifies the operator of a previous stage of rotation end of the rotation to the direction R2 of the cam member 15.

The convex portion 17q2 abuts on the inner circumferential face 15tn of the transverse site 15t2, and is fitted in the step portion 15tv by following the convex portion 17q1 as shown by the dashed lines in FIG. 11 and FIG. 12 when the cam member 15 rotates in the direction R2 to the second position, whereby the convex portion 17q2 fixes the rotation position of the cam member 15 in the second position, namely, prevents unintentional rotation of the cam member 15 to the direction R1 from the second position.

Therefore, even if the convex portion 17q2 is formed for the outer circumferential face of the transverse site 17t2, and the convex portion 17q2 is only fitted in the step portion 15tv, namely, the convex portion 17q1 is not present, the rotation position of the cam member 15 in the second position can be fixed. However, the two convex portions 17q1 and 17q2 are fitted in the step portion 15tv, whereby unintentional rotation to the direction R1 of the cam member 15 in the second position can be reliably prevented.

Note that the shape of the rocking portion 17t is not limited to the shape in which the transverse site 17t2 that extends in the direction R1 from the raised end of the raised site 17t1 is formed, and the two convex portions 17q1 and 17q2 are formed at the transverse site 17t2 to be separated in the rotational direction R, as shown in FIG. 9 to FIG. 11.

More specifically, as shown in FIG. 12, a rocking portion 17t' may be in a shape in which transverse sites 17t2' respectively extending in the rotational direction R to the direction R1 and the direction R2 from the raised end of the raised site 17t1 are formed, and at respective end portions in the rotational direction R of the transverse sites 17t2', convex portions 17q1' and 17q2' are formed.

Note that functions of the convex portions 17q1' and 17q2' are the same as the functions of the convex portions 17q1 and 17q2 shown in FIG. 9 to FIG. 11.

Note that in the bending operation apparatus 100, configurations relating to the bending operation knob 6 and the fixing knob 7 described above are similar configurations to those of the bending operation knob 4 and the fixing lever 5 except that the fixing lever 5 is replaced with the fixing knob 7, and the bending operation knob 4 is replaced with the bending operation knob 6, and therefore, the description thereof will be omitted.

Next, an operation of the present embodiment will be briefly described.

First, when the bending portion 2w of the insertion portion 2 is caused to bend in any one of the upper and the lower directions, the operator causes the bending operation knob 4 that is locked to the holding portion 35 at the upper end of the rotation shaft 18 in an unfixed state without unsteadiness to rotate in any one of the direction R1 and the direction R2 in the rotation direction R, as described above.

Further, at this time, the two movable disks 11 and 12 in the bending operation knob 4 that are positioned in the rotational direction R by the shaft member 30v of the positioning spring 30 are located in the first position shown in FIG. 5 where the movable disks 11 and 12 do not sandwich the flange portion 14f of the fixed disk 14, by the claw portions 30t of the positioning spring 30. Therefore, the fixed disk 14 rotates with the bending operation knob 4 because the O-ring 25 that is provided on the outer circumferential face of the fixed disk 14 only abuts on the inner circumferential face 4n of the bending operation knob 4 simply. Therefore, the bending operation knob 4 can be caused to rotate in the direction R1 or the direction R2 without effort.

As a result, the rotation shaft 18 fixed to the bending operation knob 4 and the sprocket 19 also rotate in the direction R1 or the direction R2, and thereby any one of the sides of the chain wound around the sprocket 19 is pulled, whereby the bending portion 2w is bent in any one of the up and the down directions. Note that at this time, the fixed shaft 10 does not rotate because the fixed shaft 10 is irrotational with respect to the rotation shaft 18.

Next, when the bending angle in any one of the up and the down directions of the bending portion 2w by the rotation operation of the bending operation knob 4 is desired to be fixed, namely, when the rotation position of the bending operation knob 4 is desired to be fixed, the operator rotates the fixing lever 5 in the direction R2 with respect to the fixed shaft 10.

As a result, the cam member 15 also rotates in the direction R2. Note that at this time, the fixed shaft 10 and the two movable disks 11 and 12 that are fixed to the fixed shaft 10 do not rotate in the direction R2.

Furthermore, in the slits 11s and 12s of the two movable disks 11 and 12, the protruding portions 15t of the cam member 15 move in the slits 11s and 12s until the end portions 11sw and 12sw of the slits 11s and 12s of the movable disks 11 and 12 abut on the end portion 15ct of the cam groove 15c.

From the above, the movable disk 11 is guided by the inclined surfaces or the circular-arc shaped surfaces formed on the cam grooves 15c, the rotational force is converted into the force in the axial direction A, and the movable disk 11 moves to the second position where the movable disk 11 separates from the movable disk 12 by having the second space d2 shorter than the first space d1, in the axial direction A, as shown in FIG. 6.

Further, with movement of the movable disk 11, the claw portions 30t of the positioning spring 30 retract into the through-hole 11k of the movable disk 11.

Further, at the time of movement to the second position from the first position, the cam member 15 rotates in the direction R2, and with this rotation, the convex portions 17q1 of the transverse sites 17t2 of the rocking portions 17t of the resistance giving member 17, which abut on the inner circumferential faces 15tn of the transverse sites 15t2 of the protruding portions 15t of the cam member 15 with an urging force are fitted in the step portions 15tv of the inner circumferential faces 15tn. Thereby, click sensing is given to the operator of the fixing lever 5, whereby the operator is notified of the previous stage of rotation end of the rotation of the cam member 15 in the direction R2.

Furthermore, when the rotation in the direction R2 of the cam member 15 advances, the convex portions 17q2 of the transverse sites 17t2 of the rocking portions 17t start to abut on the inner circumferential faces 15tn with an urging force.

Thereafter, in the second position, the flange portion 14f of the fixed disk 14 is sandwiched by the movable disks 11 and 12, and therefore, the O-ring 25 abuts on the inner circumferential face 4n of the bending operation knob 4 by a frictional force. By the frictional force, the rotation position of the bending operation knob 4 is fixed.

Furthermore, in the second position, the convex portions 17q2 of the transverse sites 17t2 of the rocking portions 17t are fitted in the step portions 15tv of the inner circumferential faces 15tn. That is, in the step portions 15tv, the convex portions 17q2 are fitted, besides the convex portions 17q1.

As a result, the position in the rotational direction R of the cam member 15, namely, the fixing lever 5 is fixed. That is, the fixing lever 5 does not move in the direction R1 of the rotation direction R from the second position unintentionally.

Next, when fixation of the rotation position of the bending operation knob 4 is desired to be released, the operator rotates the fixing lever 5 in the direction R1 with respect to the fixed shaft 10. Thereby, the cam member 15 also rotates in the direction R1.

As a result, the protruding portions 15t move in the slits 11s and 12s until the step portions 15t3 abut on the opening end portions 12sk of the slits 12s, and by the elastic force of the claw portions 30t of the aforementioned positioning spring 30, the movable disk 11 is reliably moved to the first position shown in FIG. 5 from the second position shown in FIG. 6.

Since in the above state, the flange portion 14f is not sandwiched by the movable disks 11 and 12, the bending operation knob 4 is rotatable with the fixed disk 14, and therefore, fixation of the rotation position of the bending operation knob 4 is released.

Note that the above operation is similar to operations relating to the bending operation knob 6 and the fixing knob 7.

As above, in the present embodiment, it is indicated that the resistance giving member 17 including the rocking portion 17t that abuts on the inner circumferential face 15tn of the transverse site 15t2 of the protruding portion 15t of the cam member 15 with an urging force is fixed to the outer circumferential face of the fixed shaft 10.

Further, it is indicated that in the second position, the convex portions 17q1 and 17q2 that are formed on the outer circumferential faces of the rocking portions 17t are fitted in the step portions 15W that are formed on the inner circumferential faces 15tn of the transverse sites 15t2.

Thereby, by fitting of the convex portions 17q1 and 17q2 to the step portions 15tv, the rotation position of the cam member 15, namely, the fixing lever 5 can be easily fixed, in the second position. In other words, unintentional movement of the fixing lever 5 from the second position can be prevented.

That is, by the simple configuration in which the resistance giving member 17 is only fixed to the outer circumferential face of the fixed shaft 10, unintentional movement of the fixing lever 5 from the second position can be easily prevented.

Further, due to the simple configuration in which only the resistance giving member 17 is added to the conventional configuration of the bending operation apparatus 100, assemblability is favorable.

Note that the above effects are similarly obtained for the bending operation knob 6 and the fixing knob 7.

From the above, the bending operation apparatus 100 for an endoscope that can reliably prevent unintentional motion of the fixing operation member with a simple and compact structure in which the number of components is reduced can be provided.

APPENDIX

As described in detail above, according to the embodiment of the present invention, the following configurations can be obtained. Specifically, (1) A bending operation apparatus for an endoscope that is provided in an operation portion of an endoscope, and causes a bending portion of an insertion portion of the endoscope to bend, including:

a rotatable bending operation knob that performs a bending operation of the bending portion;

a portion to be engaged that is formed in a rotation center of the bending operation knob, in an inner surface of the bending operation knob; and a rotation shaft that has a holding portion having an engaging portion that is engaged with the portion to be engaged, and a plurality of folded portions that are continuous to the engaging portion and are folded back, and abut on an outer circumferential face of the portion to be engaged, formed at an end portion in an axial direction, and is rotatable with the bending operation knob, wherein the plurality of folded portions are folded back parallel to the rotation shaft, and abut onto the outer circumferential face of the portion to be engaged from a plurality of directions in a diameter direction of the rotation shaft.

(2) The bending operation apparatus for an endoscope according to appendix 1, wherein the holding portion is formed integrally with respect to the end portion in the axial direction.

(3) The bending operation apparatus for an endoscope according to appendix 1 or 2, wherein the engaging portion is engaged with the portion to be engaged in an unfixed state.

(4) The bending operation apparatus for an endoscope according to any one of appendixes 1 to 3, wherein the respective folded portions further include extending sites that extend along a direction orthogonal to two directions that are the axial direction and the diameter direction of the rotation shaft.

(5) The bending operation apparatus for an endoscope according to any one of appendixes 1 to 4, wherein the engaging portion is at least three arm portions that extend radially in the diameter direction from an end portion of the axial direction, and slits in which the arm portions are fitted are formed in the portion to be engaged.

(6) The bending operation apparatus for an endoscope according to any one of appendixes 1 to 3, wherein a protruding portion is formed in the portion to be engaged, and the engaging portion is a hole portion in which the protruding portion is engaged and which is formed in an end portion in the axial direction.

(7) The bending operation apparatus for an endoscope according to appendix 6, wherein the respective folded portions abut on an outer circumferential face of the protruding portion with an elastic force.

(8) The bending operation apparatus for an endoscope according to any one of appendixes 1 to 7, wherein a space between an end portion in the axial direction of the folded portion and a member in the bending operation knob that faces the end portion is shorter than a length in the axial direction of the folded portion.

Incidentally, in recent years, endoscopes have been widely used in medical fields and industrial fields. The endoscopes for use in the medical field are capable of observing organs in body cavities and performing various treatments with use of treatment instruments inserted into insertion channels for the treatment instruments that are included in the endoscopes in accordance with necessity, by elongated insertion portions being inserted into the body cavities that are to be subjects.

Further, the endoscopes for use in the industrial field are capable of performing inspection such as observation of flaws, corrosion and the like of sites to be examined in objects and various treatments, by elongated insertion portions of the endoscopes being inserted into the objects such as jet engines and piping of factories.

Here, a configuration is known, in which a bending portion bendable in a plurality of directions is provided at the insertion portion of an endoscope. The bending portion not only enhances the advancing ability of the insertion portion in a crooked portion in a duct, but also makes the observation direction of an observation optical system variable, which is provided at a distal end portion located at a distal end side in an insertion direction from the bending portion, in the insertion portion.

Usually, the bending portion provided at the insertion portion of an endoscope is configured to be bendable in four directions, for example, up and down, and left and right, by a plurality of bending pieces being connected to one another along the insertion direction of the insertion portion.

Further, the bending portion is bendable in any of the directions, up and down and left and right, by a bending operation apparatus provided in the operation portion performing a pulling operation of any of the four wires that has the distal end fixed to the bending piece that is located at the most distal end side in the insertion direction out of the bending pieces, the wires being inserted through the inside of the insertion portion.

More specifically, the bending portion has a configuration in which a bending operation knob for vertical bending that is provided in the operation portion is rotationally operated, whereby a sprocket for vertical bending that is provided in the operation portion is rotated via a rotation shaft for up and down, any one of an upper side chain site and a lower side chain site of a vertical bending chain that is wound around the sprocket is pulled, whereby any one of the up and down wires is pulled, so that the bending portion is bent in either an up direction or a down direction.

Further, the bending portion has a configuration in which the bending operation knob for lateral bending that is provided in the operation portion is rotationally operated, whereby a sprocket for lateral bending that is provided in the operation portion is rotated via the rotation shaft for left and right, and any one of a left side chain site and a right side chain site of a lateral bending chain that is wound around the sprocket is pulled, whereby any one of a left and a right wires is pulled, so that the bending portion is bent in either the left direction or the right direction.

Here, the rotation shaft for up and down transmits rotation of the bending operation knob for vertical bending to the sprocket for vertical bending, and therefore, one end in the axial direction needs to be fixed to the bending operation knob for vertical bending, whereas the other end needs to be fixed to the sprocket for vertical bending.

Similarly, the rotation shaft for left and right transmits rotation of the bending operation knob for lateral bending to the sprocket for lateral bending, and therefore, one end in the axial direction needs to be fixed to the bending operation knob for lateral bending, whereas the other end needs to be fixed to the sprocket for lateral bending.

Further, usually, fixation of the respective one ends of the respective rotation shafts to the respective bending operation knobs is generally performed with use of adhesives, screws or the like, and the fixing structure like this is disclosed in, for example, Japanese Patent Application Laid-Open Publication No. 60-45377.

However, when screws are used in fixation of the rotation shafts as in the fixing structure disclosed in Japanese Patent Application Laid-Open Publication No. 60-45377, such a structure is adopted that the one ends of the respective rotation shafts are fixed to other members different from the rotation shafts by screws, and the other members are fixed to the respective bending operation knobs with adhesives, screws or the like, whereby the other members have to additionally be used in fixation of the respective rotation shafts, and therefore, the problem arises that the respective bending operation knobs are increased in size.

Further, when an adhesive or a screw is used in fixation of a rotation shaft, fixing work takes time, and therefore, the problem that the work cost increases arises.

Therefore, such a configuration is also conceivable which transmits rotation of the respective bending operation knobs to the respective rotation shafts by fitting the one ends of the respective rotation shafts onto the respective bending operation knobs, namely, in an unfixed state, without use of an adhesive or a screw.

However, the above configuration has not only the problem that fitting unsteadiness of the respective bending operation knobs to the one ends of the respective rotation shafts become large, namely, the respective bending operation knobs are inclinedly assembled to the one ends of the respective rotation shafts, but also the problem that when the bending operation knobs are distributed as units, together with the rotation shafts, the rotation shafts are detached from the operation knobs, and therefore handling thereof is difficult.

The present appendixes are made in the light of the above-described problems, and has an object to provide a bending operation apparatus for an endoscope that is excellent in assemblability, capable of realizing miniaturization of bending operation knobs, and is further capable of assembling rotation shafts to the bending operation knobs without unsteadiness, with a simple configuration.

Further, as described in detail above, according to the embodiment of the present invention, a configuration as follows can be obtained. Specifically, (9) A bending operation apparatus for an endoscope, including:

a rotation shaft;

a bending operation knob that is rotatable with the rotation shaft, and performs a bending operation of a bending portion of an endoscope;

a fixed shaft that is provided on a same axis as the rotation shaft in an axial direction of the rotation shaft, and is irrotational with respect to the rotation shaft;

two movable disks that are fixed to an outer periphery in a diameter direction of the fixed shaft, and are movable to a first position where the two movable disks are separated by having a first space, and to a second position where the two movable disks are separated by having a second space that is shorter than the first space, in the axial direction;

holes that are formed in the respective movable disks, in which the fixed shaft is fitted, with shapes, when seen in a plan view, having polygonal shapes;

a fixed disk that is provided on a same axis in the axial direction as the two movable disks, abuts on an inner circumferential face of the bending operation knob, and gives a frictional force to rotation of the bending operation knob by being sandwiched by the two movable disks in the second position; and a positioning spring that is fitted along the axial direction in between the hole of the one movable disk and the hole of the other movable disk, and an outer periphery of the fixed shaft, wherein the positioning spring has a shaft member along the axial direction that performs positioning in a rotational direction of the rotation shaft of the other movable disk to the one movable disk, and a claw portion that protrudes from an outer circumferential face in the shaft member to an outer side in a diameter direction between the one movable disk and the other movable disk, and that is elastically deformable in the diameter direction, and the claw portion causes the respective movable disks to separate to the first position from the second position by an elastic force.

(10) The bending operation apparatus for an endoscope according to appendix 9, wherein when the movable disks are moved to the second position, the claw portion retracts to an inner side in the diameter direction by movement of one of the movable disks, and is located in the hole of the one movable disk.

Incidentally, in recent years, endoscopes have been widely used in medical fields and industrial fields. The endoscopes for use in the medical field are capable of observing organs in body cavities and performing various treatments with use of treatment instruments inserted into insertion channels for the treatment instruments that are included in the endoscopes in accordance with necessity, by elongated insertion portions being inserted into body cavities that are to be subjects.

Further, the endoscopes for use in the industrial field are capable of performing inspection such as observation of flaws, corrosion and the like of sites to be examined in objects and various treatments, by elongated insertion portions of the endoscopes being inserted into the objects such as jet engines and piping of factories.

Here, a configuration is known, in which a bending portion bendable in a plurality of directions is provided at the insertion portion of an endoscope. The bending portion not only enhances the advancing ability of the insertion portion in a crooked portion in a duct, but also makes the observation direction of an observation optical system variable, which is provided at a distal end portion located at a distal end side in an insertion direction from the bending portion, in the insertion portion.

Usually, the bending portion provided at the insertion portion of an endoscope is configured to be bendable in four directions, for example, up and down, and left and right, by a plurality of bending pieces being connected to one another along the insertion direction of the insertion portion.

Further, the bending portion is bendable in any of the directions, up and down and left and right, by a bending operation apparatus provided in the operation portion performing a pulling operation of any of the four wires that has the distal end fixed to the bending piece that is located at the most distal end side in the insertion direction out of the bending pieces, the wires being inserted through the inside of the insertion portion.

More specifically, the bending portion has a configuration in which a bending operation knob for vertical bending that is provided in the operation portion is rotationally operated, whereby a sprocket for vertical bending that is provided in the operation portion is rotated, any one of an upper side chain site and a lower side chain site of a vertical bending chain that is wound around the sprocket is pulled, whereby any one of the up and down wires is pulled, so that the bending portion is bent in either an up direction or a down direction.

Further, the bending portion has a configuration in which the bending operation knob for lateral bending that is provided in the operation portion is rotationally operated, whereby a sprocket for lateral bending that is provided in the operation portion is rotated, and any one of a left side chain site and a right side chain site of a lateral winding chain that is wound around the sprocket is pulled, whereby any one of left and right wires is pulled, so that the bending portion is bent in either the left direction or the right direction.

Further, a configuration is known, in which the operation portion is provided with a vertical fixing lock lever that fixes the bending angle of the bending portion that is bent in the up direction or the down direction by the rotational operation of the bending operation knob for vertical bending, namely, the rotation position of the bending operation knob for vertical bending, and a lateral fixing lock knob that fixes the bending angle of the bending portion that is bent in the left direction or the right direction by the rotational operation of the bending operation knob for lateral bending, namely, the rotation position of the bending operation knob for lateral bending, and the configuration is disclosed in, for example, Japanese Patent Application Laid-Open Publication No. 10-286220.

Japanese Patent Application Laid-Open Publication No. 10-286220 discloses the configuration in which in the clearance in the bending operation knob for vertical bending, a friction member that abuts on the inner circumferential surface of the knob, and a movable member and a fixed member that are capable of sandwiching the friction member, and that are fixed to a vertical fixing lock lever are provided.

When the rotation position of the bending operation knob for vertical bending is fixed with use of the configuration disclosed in Japanese Patent Application Laid-Open Publication No. 10-286220, the vertical fixing lock lever is rotated in one direction, and with the lock lever, the movable member is rotated in one direction, whereby the movable member is moved with respect to the fixed member with use of a screw mechanism, the friction member is sandwiched between the fixed member and the movable member to be elastically deformed, and the friction member is caused to abut on the inner circumferential face of the bending operation knob for vertical bending by a frictional force. Thereby, the rotation position of the bending operation knob for vertical bending is fixed by the frictional force.

Note that in Japanese Patent Application Laid-Open Publication No. 10-286220, the configuration that fixes the rotation position of the bending operation knob for lateral bending also has the similar configuration to the configuration that fixes the rotation position of the bending operation knob for vertical bending.

However, in the configuration disclosed in Japanese Patent Application Laid-Open Publication No. 10-286220, which is a configuration that elastically deforms the frictional member by sandwiching the friction member by the movable member and the fixed member by the screw mechanism, the friction member easily deteriorates with a plurality of times of elastic deformation, and as a result, the problem arises that after a plurality of times of use, the frictional force of the friction member to the inner circumferential face of the bending operation knob is reduced, namely, the frictional force of the friction member varies.

Further, in order to elastically deform the friction member, the friction member has to be sandwiched by the fixed member and the movable member with a large force, and therefore, the problem arises that the lock lever and the lock knob that rotate the movable member have to be rotated with a large force.

Thus, such a configuration is known that can reliably sandwich the fixed disk that is caused to abut on the inner circumferential face of the bending operation knob by a frictional force with two movable disks even if the fixing operation member is rotated with a small force, with use of a cam member without using a screw mechanism or the like.

However, in the configuration that sandwiches the fixed disk by the two movable disks with use of a cam member or the like, the two movable disks are difficult to separate from the fixed disk even if the fixing operation members are rotated in the opposite direction from fixation, when fixation of the rotation position of the respective bending operation knobs using the vertical fixing lock lever and the lateral fixing lock knob (hereinafter, collectively called the fixing operation member) is not required, and as a result, an unnecessary frictional force is given to the inner circumferential face of the bending operation knob from the fixed disk, and therefore, the problem arises that unnecessary resistance occurs to the rotation operations of the respective bending operation knobs.

Furthermore, in the configuration that moves the two movable disks with use of a cam member or the like, a problem exists that positioning in the rotational direction of the bending operation knob, of one movable disk to the other movable disk is difficult at the time of assembly, more specifically, that when the two movable disks are fitted in the fixed shaft, positioning of the fitting holes of the respective movable disks to the fixed shaft is difficult.

The present appendixes are made in the light of the above described problems, and has an object to provide a bending operation apparatus for an endoscope capable of reliably separating two movable disks from a fixed disk, and capable of easily performing positioning of the two movable disks, with a simple configuration.

What is claimed is:

1. A bending operation apparatus for an endoscope, comprising:
    a rotation shaft;
    a bending operation knob that is rotatable with the rotation shaft, and performs a bending operation of a bending portion of an endoscope;
    a fixed shaft that is provided on a same axis as the rotation shaft in an axial direction of the rotation shaft, and is irrotational with respect to the rotation shaft;
    a fixed disk that includes a first surface and a second surface, and rotates with rotation of the bending operation knob;
    two movable disks including a first movable disk provided at a side of the first surface of the fixed disk, and a second movable disk provided at a side of the second surface of the fixed disk;
    a moving member that is located on a same axis in the axial direction as the two movable disks, and moves, the first movable disk or the second movable disk to a first position where the two movable disks are separated by a first space by rotation of the moving member, and a second position where the two movable disks are separated by a second space that is shorter than the first space and at which the two movable disks sandwich the fixed disk by respectively abutting on the fixed disk;
    a resistance giving member that is fixed to an outer periphery of the fixed shaft, is provided in an inner side of the moving member, and gives a resistance force to rotation of the moving member; and a fixing operation member that performs a rotational operation of the moving member, wherein the resistance giving member has a rocking portion that fixes a rotation position of the moving member in the second position of the movable disk by abutting onto an inner circumferential face of a protruding portion provided at the moving member that moves with the rotation of the moving member, with an urging force, and is rockable in a diameter direction of the moving member.

2. The bending operation apparatus for an endoscope according to claim 1, wherein the rocking portion is configured by an elastic member that is rockable in the diameter direction.

3. The bending operation apparatus for an endoscope according to claim 1, wherein the moving member is a ring-shaped member that rotates with a center axis of the rotation shaft and the fixed shaft as a center by the fixing operation member being rotationally operated.

4. The bending operation apparatus for an endoscope according to claim 3, wherein slits that penetrate in the axial direction are respectively formed in the two movable disks, and the moving member is a cam member that has the protruding portion that penetrates through the respective slits in the axial direction, the protruding portion being movable in a rotational direction of the rotation shaft in the respective slits, is rotatable in the rotational direction separately from the rotation of the rotation shaft, and causes the two movable disks to move to the second position from the first position by a cam groove formed in the protruding portion, with rotation in one direction.

5. The bending operation apparatus for an endoscope according to claim 4, wherein the rocking portion fixes a rotation position of the cam member in the second position of the movable disk by abutting onto an inner circumferential face of the protruding portion of the cam member that moves with the rotation in the one direction of the cam member, with an urging force.

6. The bending operation apparatus for an endoscope according to claim 5, wherein the protruding portion has a transverse site along the rotational direction, and the rocking portion abuts on an inner circumferential face of the transverse site that moves with the rotation in the one direction of the cam member.

7. The bending operation apparatus for an endoscope according to claim 4, wherein the protruding portion has a transverse site along the rotational direction, and the rocking portion is formed to be elongated along the rotational direction to face the transverse site.

8. The bending operation apparatus for an endoscope according to claim 7, wherein a convex portion is formed at the rocking portion, and a step portion is formed at the inner circumferential face of the transverse site, and the convex portion is fitted in the step portion in the second position so as to fix the rotation position of the cam member in the second position.

9. The bending operation apparatus for an endoscope according to claim 8, wherein two of the convex portions are formed to be separated in the rotational direction with respect to the rocking portion.

10. The bending operation apparatus for an endoscope according to claim 9, wherein out of the two convex portions, by the convex portion that is fitted in the step portion of the transverse site later, with the rotation in the one direction of the cam member, the rotation position of the cam member is fixed in the second position.

\* \* \* \* \*